US012702370B2

(12) United States Patent
Martinez Ferreira et al.

(10) Patent No.: US 12,702,370 B2
(45) Date of Patent: Aug. 11, 2026

(54) MEDICAL IMAGING SYSTEM CABLE

(71) Applicant: GE Precision Healthcare LLC, Waukesha, WI (US)

(72) Inventors: Carlos Martinez Ferreira, Buc (FR); Bernard Bouvier, Buc (FR)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 198 days.

(21) Appl. No.: 18/625,113

(22) Filed: Apr. 2, 2024

(65) Prior Publication Data

US 2025/0134480 A1 May 1, 2025

Related U.S. Application Data

(60) Provisional application No. 63/593,899, filed on Oct. 27, 2023.

(51) Int. Cl.
*A61B 6/00* (2006.01)
*H02G 11/00* (2006.01)

(52) U.S. Cl.
CPC ......... *A61B 6/4441* (2013.01); *H02G 11/006* (2013.01)

(58) Field of Classification Search
CPC ........... A61B 6/4441; A61B 6/56; A61B 6/44; A61B 6/4417; A61B 6/4429; A61B 6/54; H02G 11/006
See application file for complete search history.

(56) References Cited

U.S. PATENT DOCUMENTS

2002/0017428 A1* 2/2002 Mauthner ................ A62B 1/14 182/5
2019/0029620 A1* 1/2019 Baumann ............. B25J 19/0025
2021/0085264 A1* 3/2021 Cleary ................. A61B 6/4441

FOREIGN PATENT DOCUMENTS

CN 209361135 U * 6/2018 ............... A61G 7/00
GB 2610552 A * 3/2023 ............. H02G 11/02

* cited by examiner

*Primary Examiner* — Uzma Alam
*Assistant Examiner* — Fani Polyzos Boosalis
(74) *Attorney, Agent, or Firm* — McCoy Russell LLP

(57) ABSTRACT

Systems are provided for a medical imaging system. In one example, the medical imaging system includes a C-arc with a radiation source coupled to a first end and a detector coupled to a second end of the C-arc, opposite to the radiation source, where the detector is configured to receive radiation from the radiation source The medical imaging system further includes a pivot arm configured to adjust a position of the C-arc and a cable chain coupled to each of the C-arc and the pivot arm via rotatable joints wherein the cable chain extends upwardly from each of the rotatable joints at each of a plurality of positions of the C-arc.

15 Claims, 17 Drawing Sheets

MEDICAL IMAGING SYSTEM CABLE

CROSS REFERENCE TO RELATED APPLICATIONS

This application claims priority to U.S. Provisional Patent Application No. 63/593,899, titled "MEDICAL IMAGING SYSTEM CABLE," and filed Oct. 27, 2023, the entire contents of which is hereby incorporated by reference for all purposes.

FIELD

Embodiments of the subject matter disclosed herein relate to a cable for medical imaging systems, and more particularly, to a cable for medical imaging systems including a C-shaped gantry.

BACKGROUND

Radiographic imaging systems may be used in various applications, including medical and industrial applications. In a medical environment, a radiographic imaging system may provide a non-invasive means of imaging tissue and bone of a patient. Some radiographic imaging systems may comprise a rotatable, curved arm, referred to as a C-arc, coupled to a base unit. The C-arc may include an x-ray source positioned at one end and a detector positioned at another end. A clearance may be provided between the x-ray source and the detector to receive an object, such as a portion of the patient's body, which may be irradiated with radiation from the x-ray source. Upon irradiating the object, the x-ray radiation penetrates through the object and is captured by the detector. By penetrating the object placed between the source and detector, the x-rays enable an image of the object to be captured and relayed to the display monitor, where the image may be displayed or stored and retrieved later.

BRIEF DESCRIPTION

In one example, the medical imaging system includes a C-arc with a radiation source coupled to a first end and a detector coupled to a second end of the C-arc, opposite to the radiation source, where the detector is configured to receive radiation from the radiation source. The medical imaging system further includes a pivot arm configured to adjust a position of the C-arc and a cable chain coupled to each of the C-arc and the pivot arm via rotatable joints wherein the cable chain extends upwardly from each of the rotatable joints at each of a plurality of positions of the C-arc.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 5:
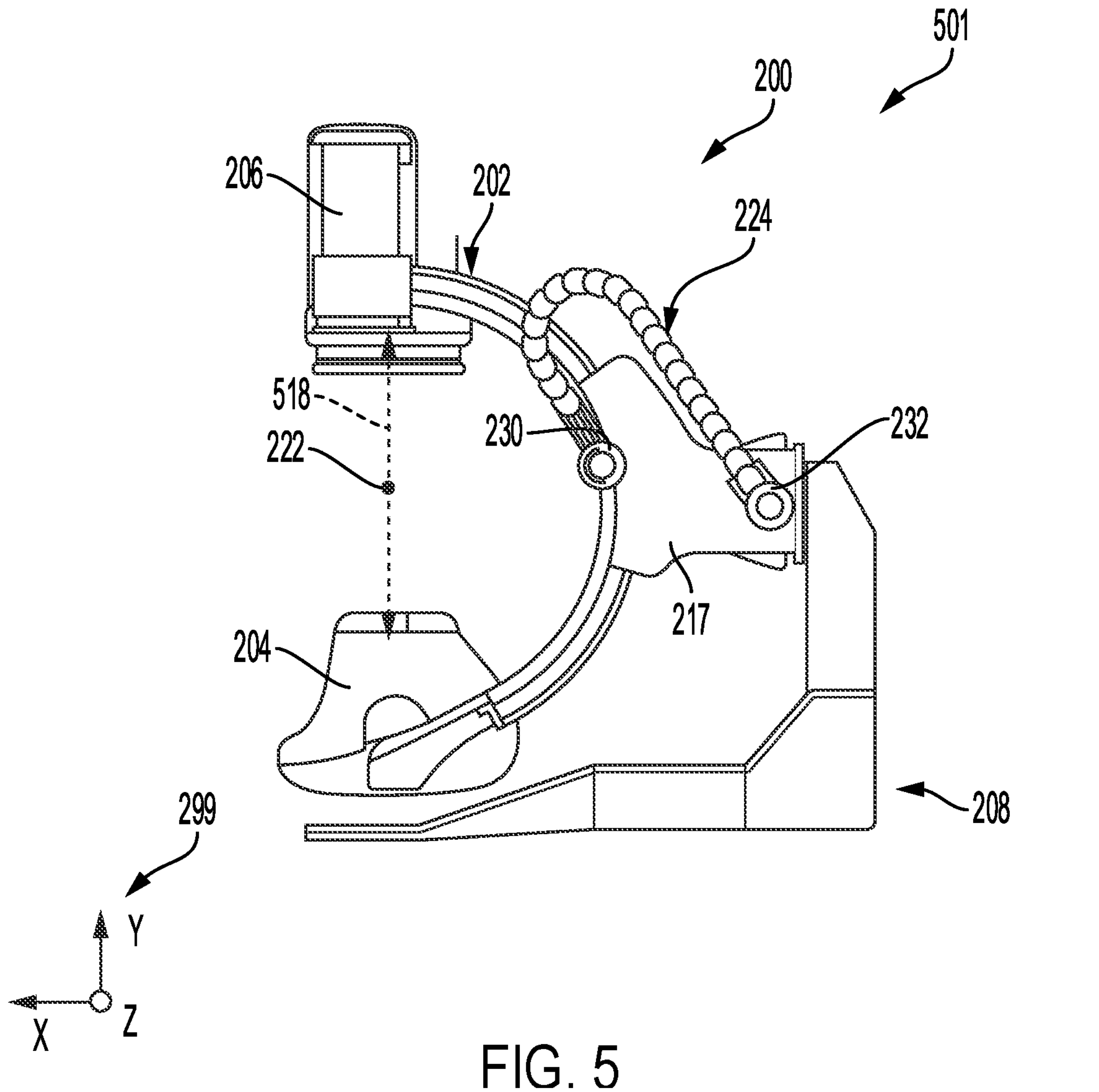
FIGS. 5-7 show the C-arc and cable chain in various positions.
Figure 6:
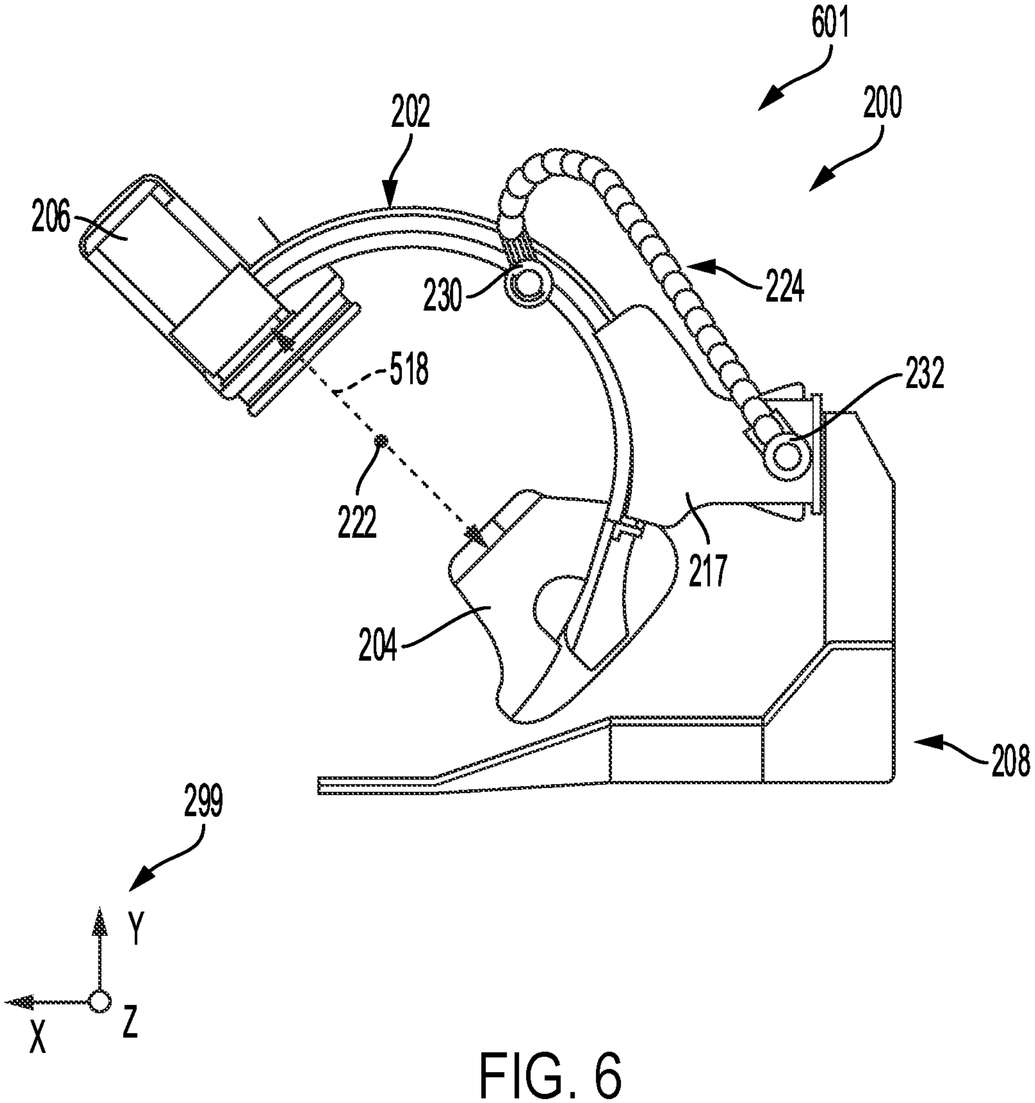
Figure 7:
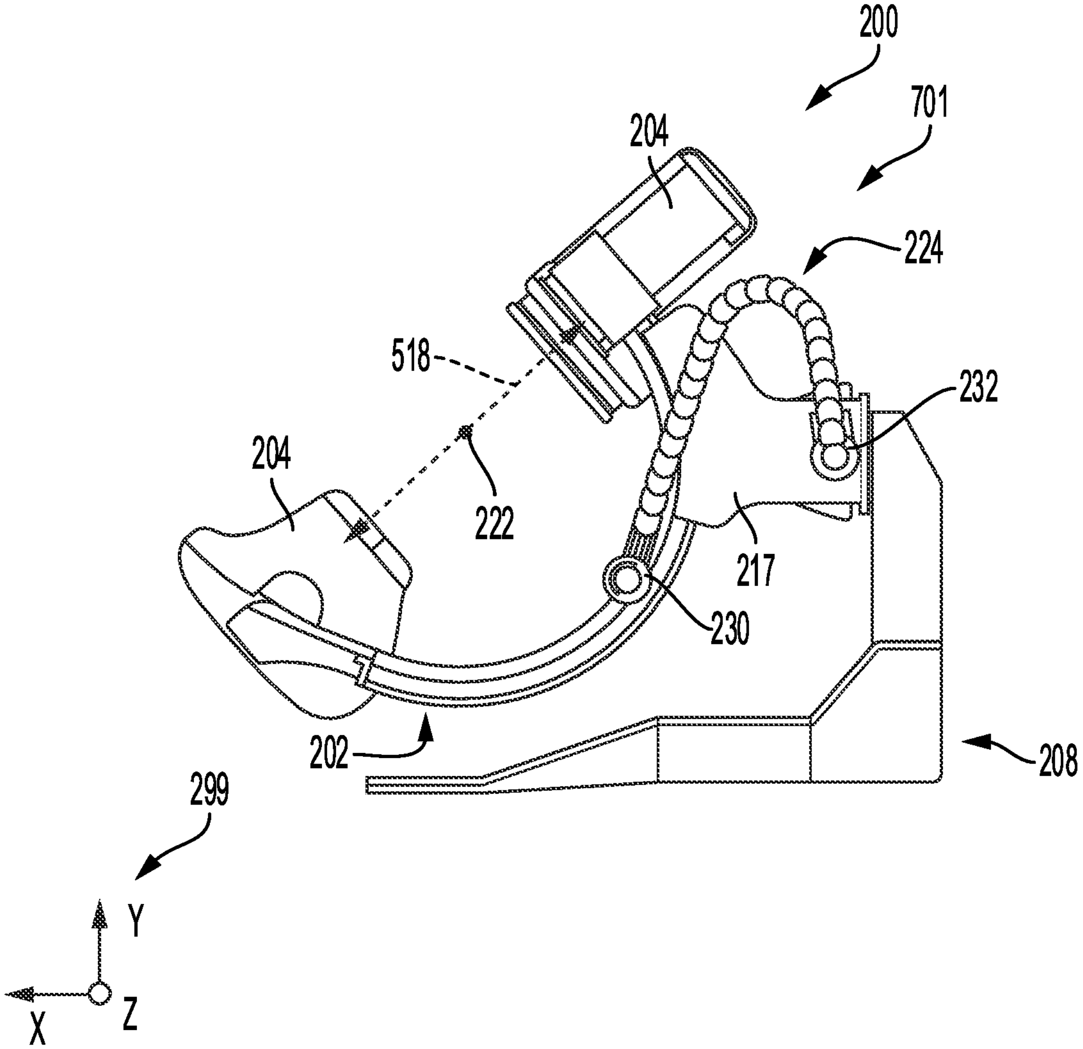

The following description relates to various embodiments for a medical imaging system. The medical imaging system, such as the medical imaging system shown by FIGS. 1-7, includes a C-arc. A radiation source is arranged at a first end of the C-arc and a radiation detector is arranged at an opposing, second end of the C-arc. A subject to be imaged by the medical imaging system may be arranged between the radiation source and the radiation detector. The radiation source may emit radiation, such as x-ray radiation, and the radiation may pass through the subject, with attenuated x-ray radiation that has passed through the subject intercepted, or received, by the detector. During imaging, the C-arc may be oriented in more than one position, as shown in FIGS. 5-7, such that radiation may pass through the subject at multiple different angles.

Figure 8:
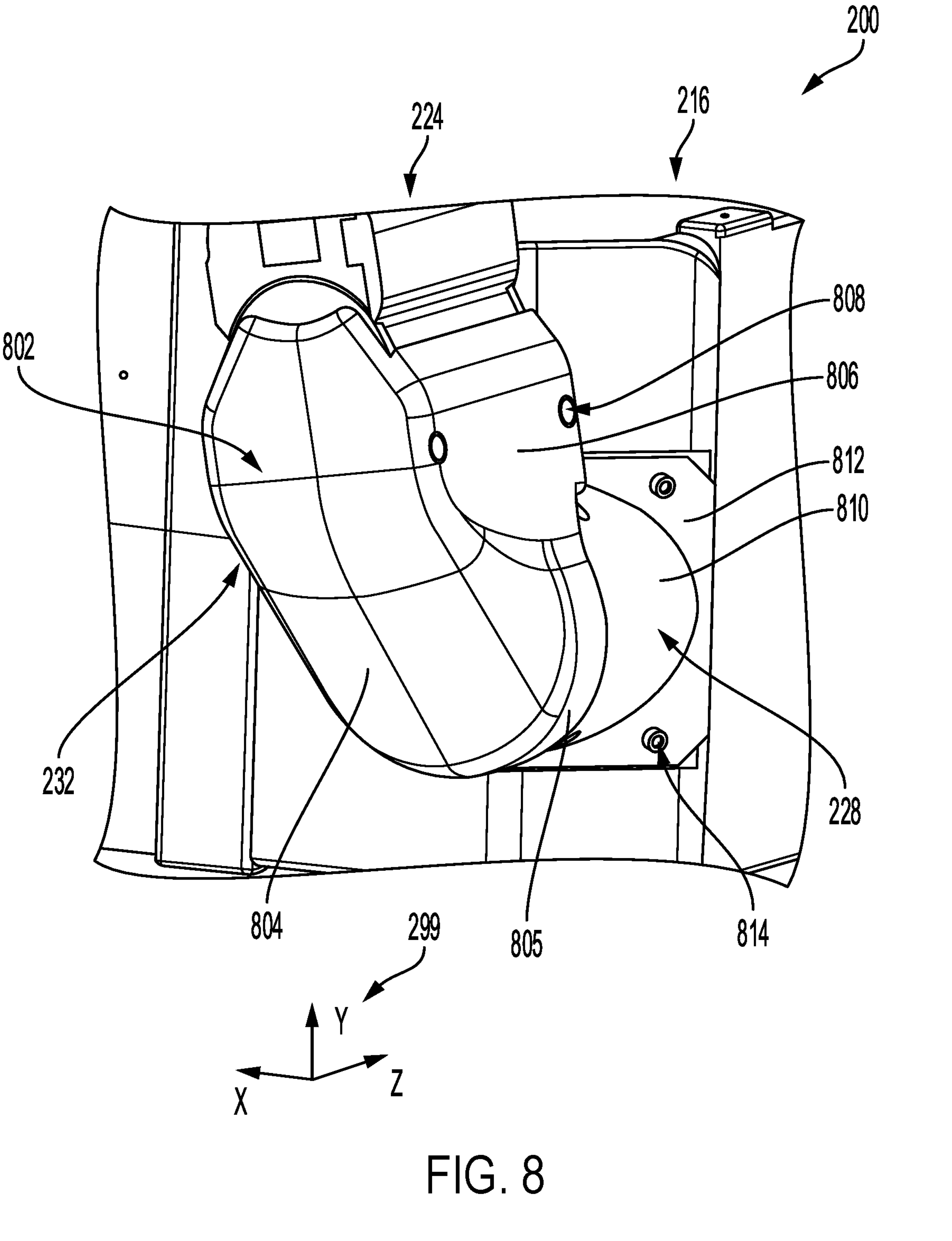
FIG. 8 shows a cable chain joint including a joint cover coupled to a cable chain joint mount.
Figure 13:
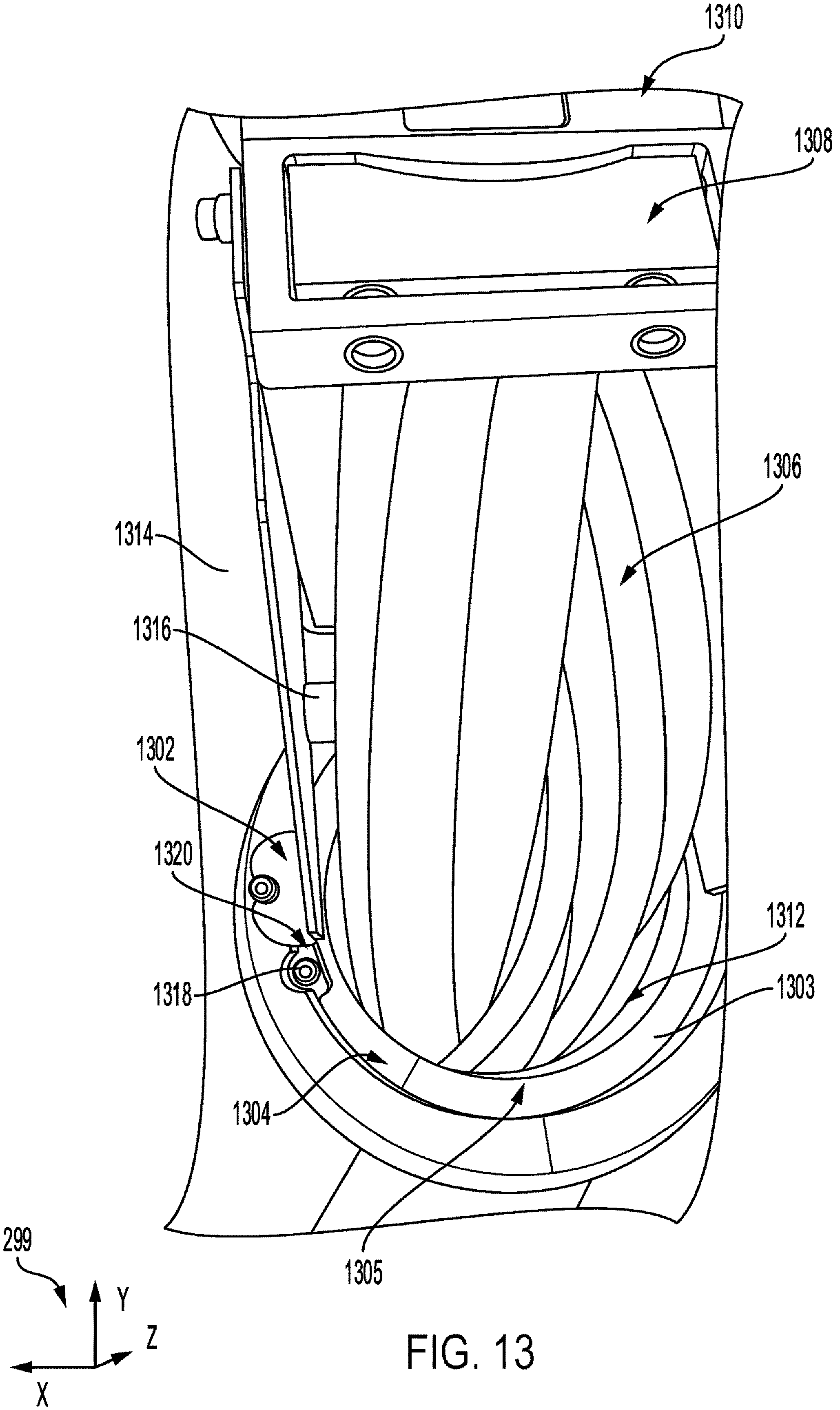
FIG. 13 shows a cable chain joint mount and a portion of a cable chain joint accommodating a plurality of cables.
Figure 14:
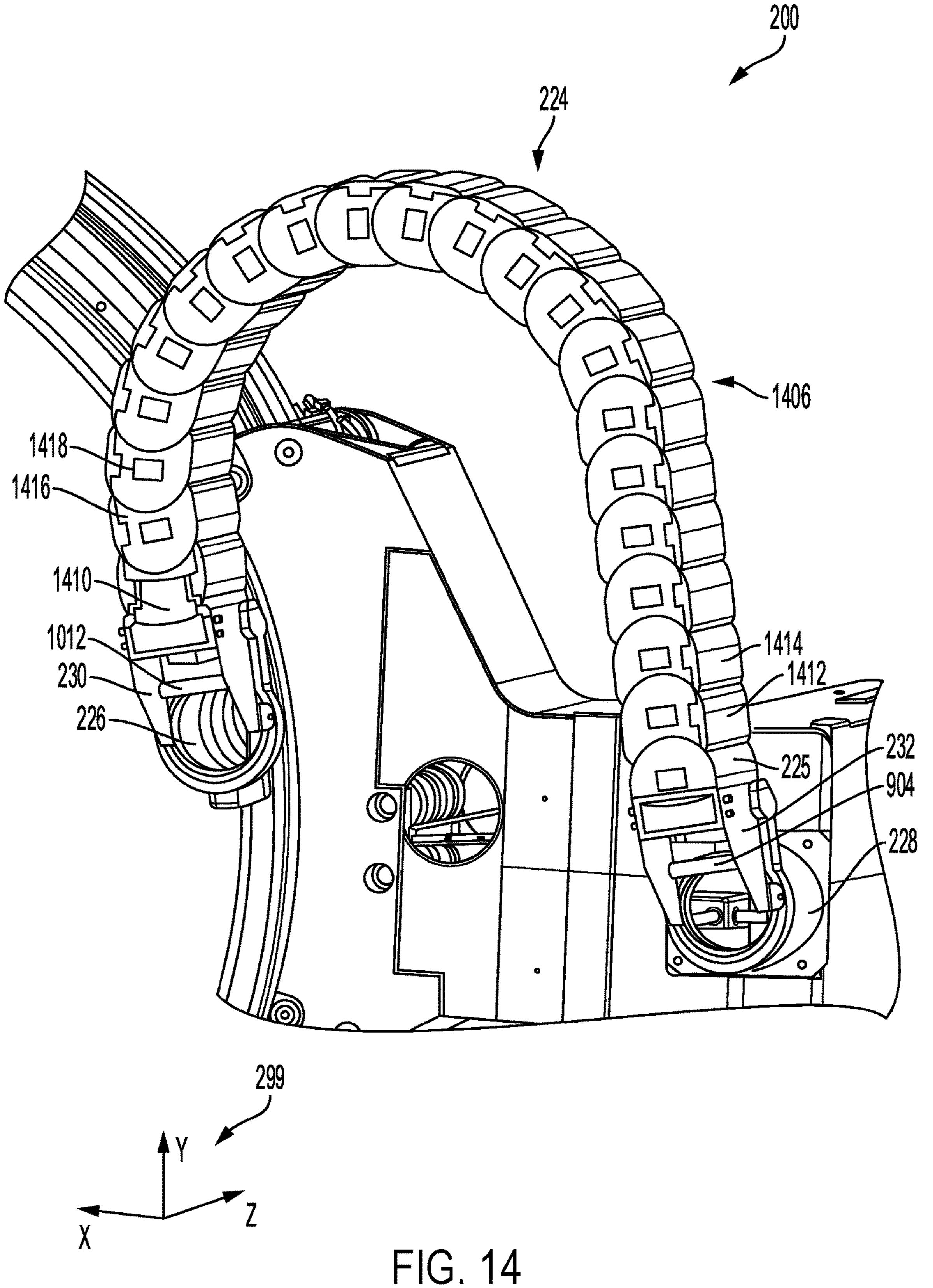
FIG. 14 shows the cable chain with two cable chain joints coupled to the medical imaging system.
Figure 15:
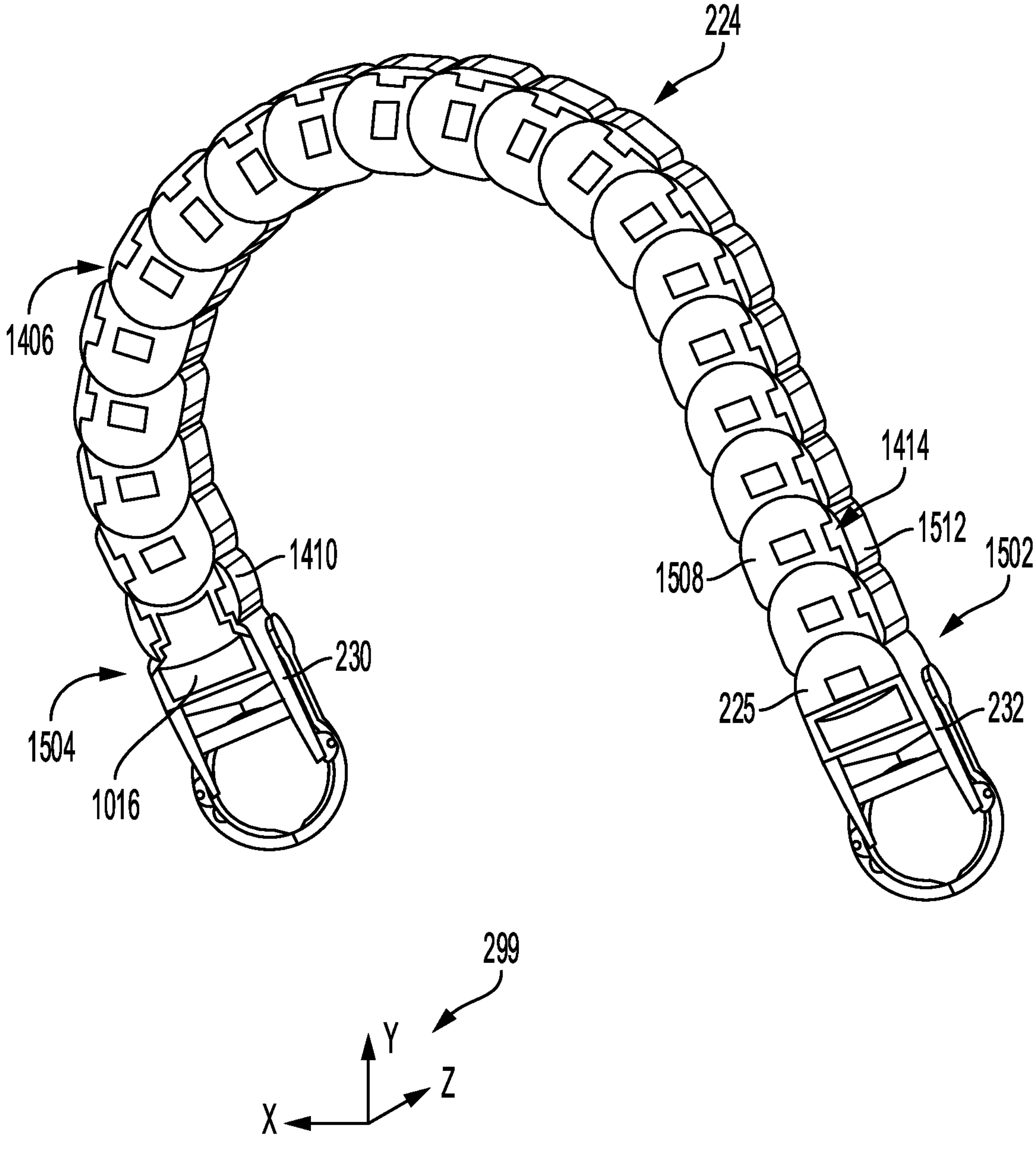
FIG. 15 shows a first view of the cable chain including two cable chain joints.
Figure 16:
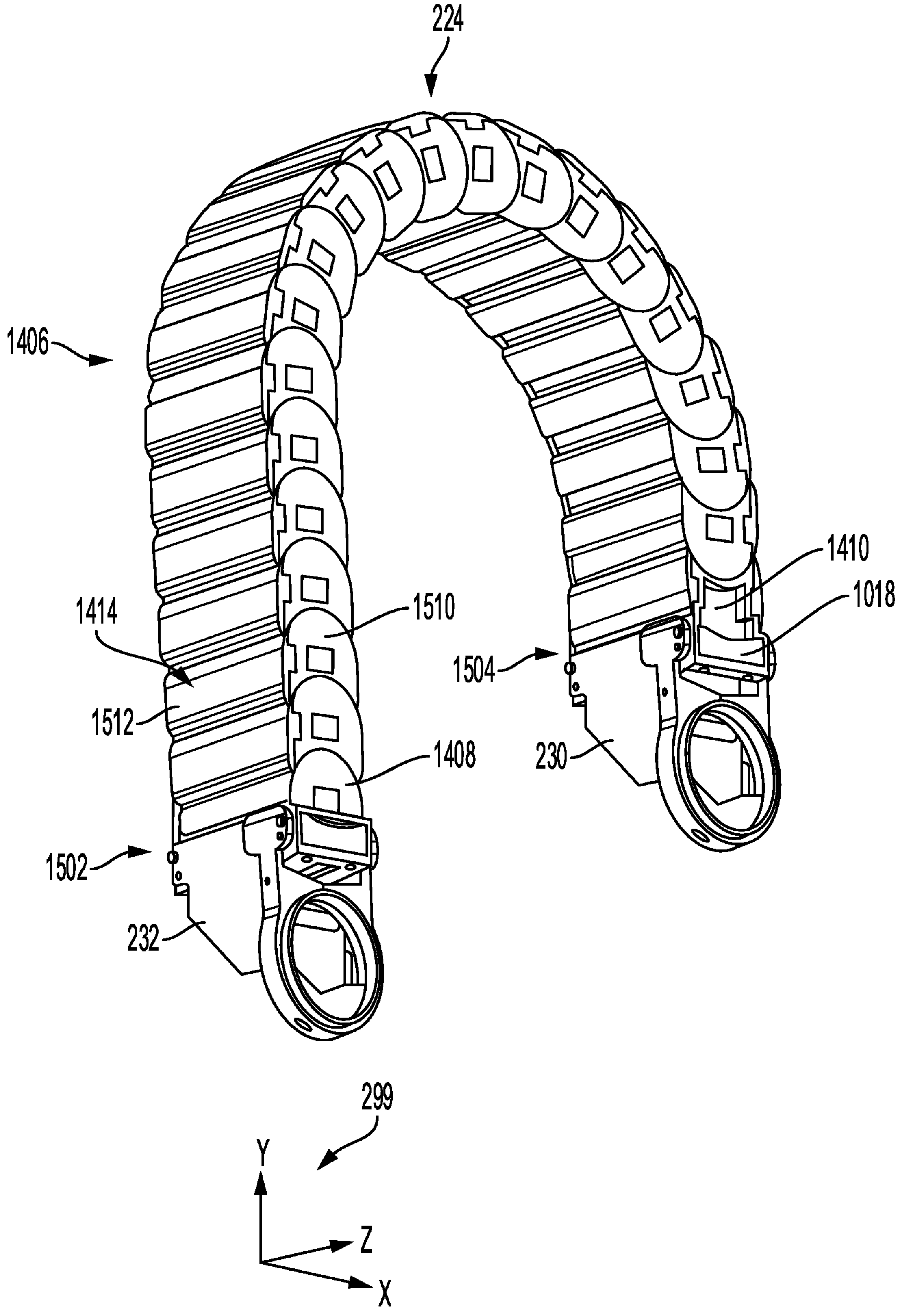
FIG. 16 shows a second view of the cable chain of FIG. 15.
Figure 17:
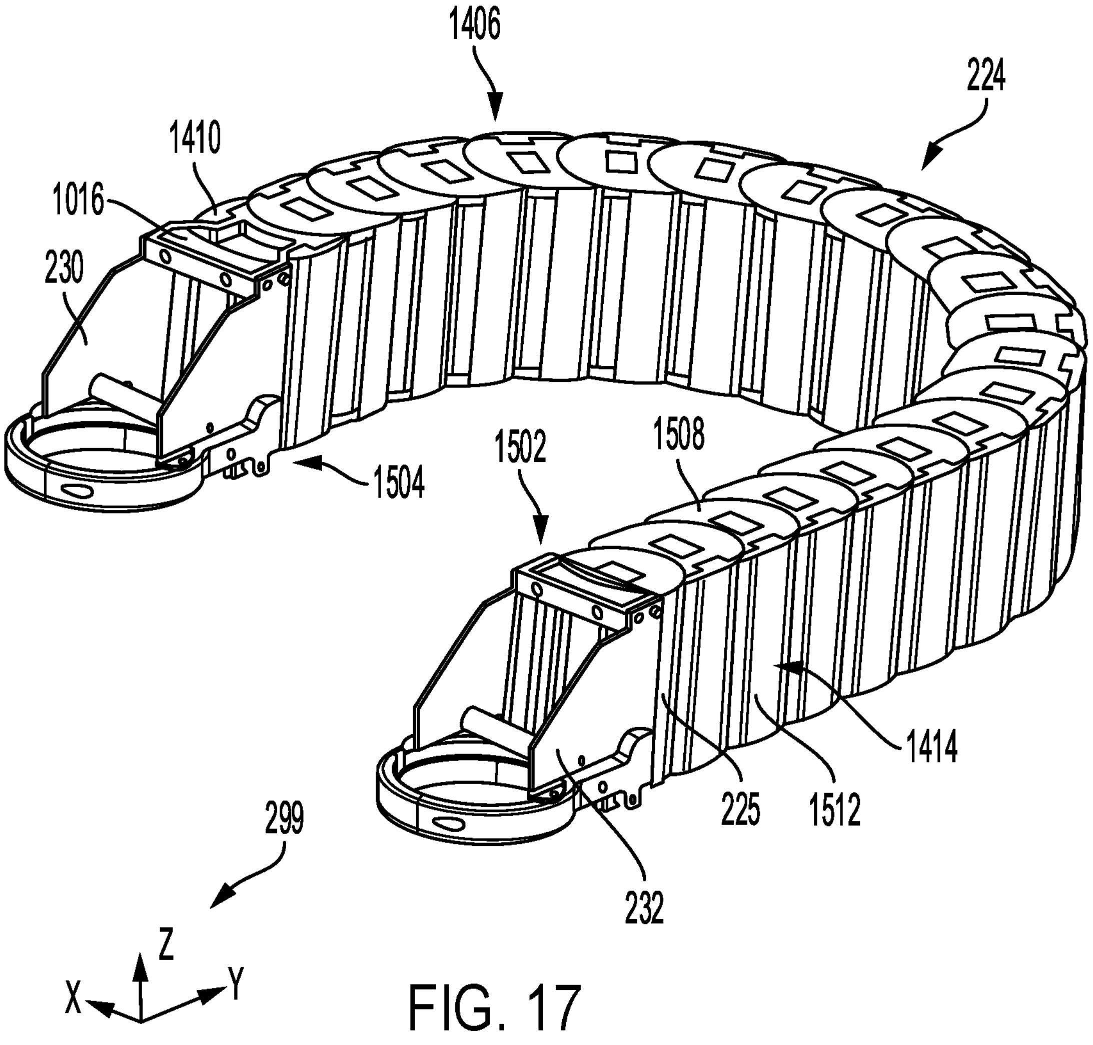
FIG. 17 shows a third view of the cable chain of FIG. 15.

The medical imaging system may include a cable management system that includes a cable chain, as shown in FIGS. 15-17, configured to house one or more electrical cables of the medical imaging system. The cable chain may be coupled to the medical imaging system via pivotable joints of the cable management system that couple to respective joint mounts of the medical imaging system, as shown in FIGS. 8 and 14. Magnified views of the pivotable joints and joint mounts are shown in FIGS. 9-12. The cables may pass through the pivotable joints and joint mounts, as shown in FIG. 13. FIGS. 2-4 and 8-17 are shown to scale, though other relative dimensions may be used.

Figure 1:
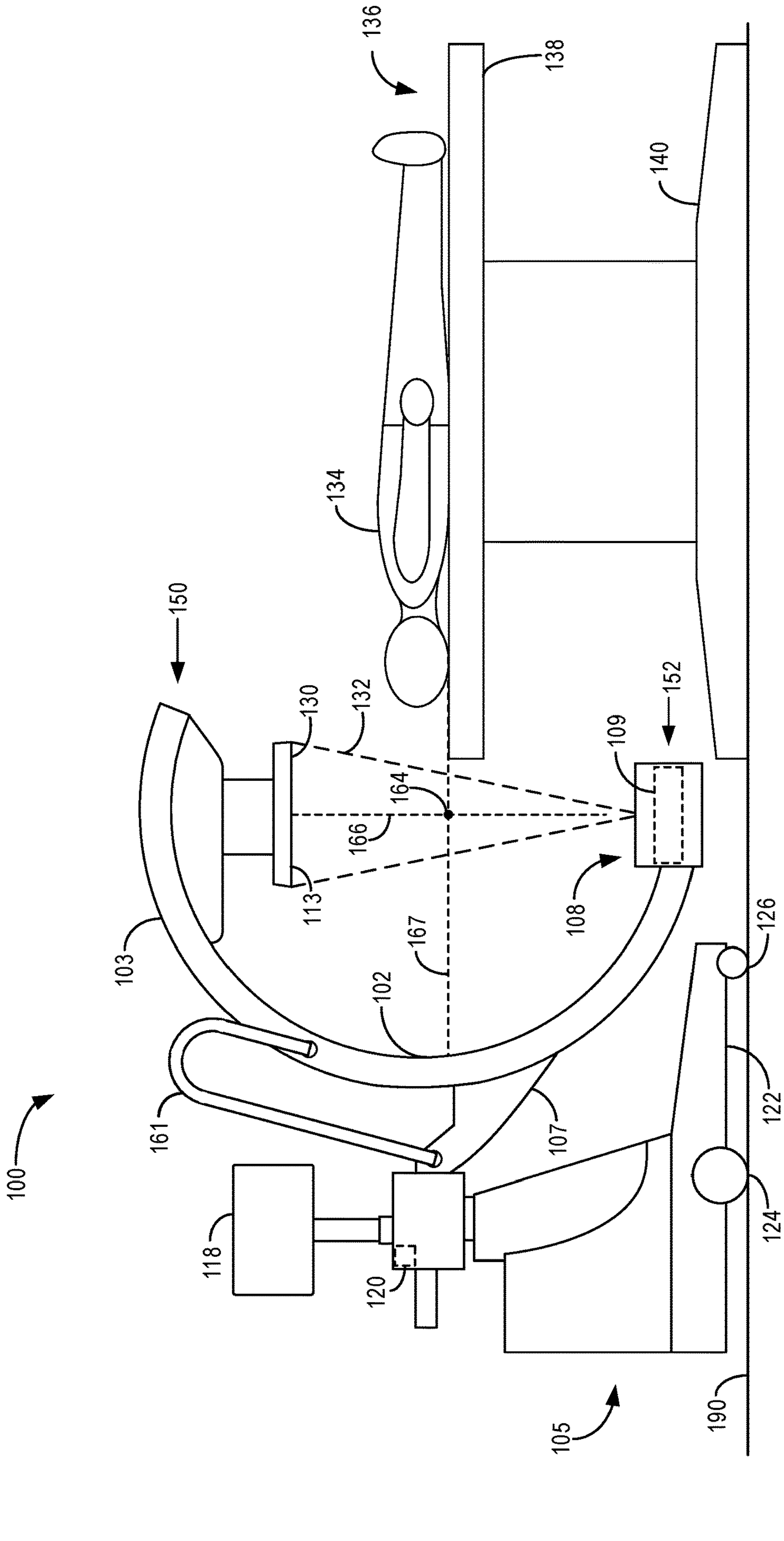
FIG. 1 shows an example medical imaging system including a C-arc.

Referring to FIG. 1, an imaging system 100 including a C-arc 102 (which may also be referred to a C-shaped gantry or a C-arm) is schematically shown. Imaging system 100 may be referred to herein as a medical imaging system and/or C-arc imaging system. The imaging system 100 includes a radiation source, and in the examples described herein, the radiation source is an x-ray unit 108 (which may be referred to herein as an x-ray tube) positioned opposite to detector 130 (which may be referred to herein as an x-ray detector) and configured to emit x-ray radiation. In other examples, the radiation source may be configured to emit a different type of radiation for imaging (e.g., imaging a subject, such as patient 134), such as gamma rays, and the detector (e.g., x-ray detector 130) may be configured to detect the radiation emitted by the radiation source (e.g., x-ray beam 132). The imaging system 100 additionally includes base unit 105 supporting imaging system 100 on ground surface 190 on which the imaging system 100 sits (e.g., via base 122 supported by wheel 124, wheel 126, etc.).

The C-arc 102 includes a C-shaped portion 103 connected to an extended portion 107, with the extended portion 107 rotatably coupled to the base unit 105. The detector 130 is coupled to the C-shaped portion 103 at a first end 150 of the C-shaped portion 103, and the x-ray unit 108 is coupled to the C-shaped portion 103 at an opposing, second end 152 of the C-shaped portion 103. As an example, the C-arc 102 may be configured to rotate at least 180 degrees in opposing directions relative to the base unit 105. The C-arc 102 is rotatable about at least a rotational axis 164 and may additionally rotate about axis 167. The C-shaped portion 103 may be rotated as described above in order to adjust the x-ray unit 108 and detector 130 (positioned on opposite ends of the C-shaped portion of the C-arc 102 along axis 166, where axis 166 intersects rotational axis 164 and extends radially relative to rotational axis 164) through a plurality of positions.

During an imaging operation (e.g., a scan), a portion of a patient's body placed in an opening formed between the x-ray unit 108 and detector 130 may be irradiated with radiation from the x-ray unit 108. For example, patient 134 may be supported by a patient support table 136, with the patient support table 136 including a support surface 138 and base 140, and may be arranged between the x-ray unit 108 and the detector 130. The x-ray unit 108 includes an x-ray tube insert 109 and x-ray radiation generated by the x-ray tube insert 109 may emit from the x-ray unit 108. The radiation may penetrate the portion of the patient's body arranged to be irradiated and may travel to the detector 130 where the radiation is captured (e.g., intercepted by a detector surface 113 of the detector 130). By penetrating the portion of the patient's body placed between the x-ray unit 108 and detector 130, an image of the patient's body is captured and relayed to an electronic controller 120 of the imaging system 100 (e.g., via an electrical connection line, such as electrically conductive cable 161). The image may be displayed via display device 118. Images of the subject acquired by the imaging system 100 via the x-ray unit 108 and the detector 130 as described above may be referred to herein as projection images and/or scan projection images.

The base unit 105 may include the electronic controller (e.g., a control and computing unit) that processes instructions or commands sent from the user input devices during operation of the imaging system 100. The base unit 105 may also include an internal power source (not shown) that provides electrical power to operate the imaging system 100. Alternatively, the base unit 105 may be connected to an external electrical power source to power the imaging system 100. A plurality of connection lines (e.g., electrical cables, such as electrically conductive cable 161) may be provided to transmit electrical power, instructions, and/or data between the x-ray unit 108, detector 130, and the control and computing unit. The plurality of connection lines may transmit electrical power from the electrical power source (e.g., internal and/or external source) to the x-ray unit 108 and detector 130.

The C-arc 102 may be adjusted to a plurality of different positions by rotation of the C-shaped portion 103 of the C-arc 102. For example, in an initial, first position shown by FIG. 1, the detector 130 may be positioned vertically above the x-ray unit 108 relative to a ground surface 190 on which the imaging system 100 sits, with axis 166 arranged normal to the ground surface 190 intersecting a midpoint of each of the outlet of x-ray unit 108 and detector surface 113 of detector 130. The C-arc 102 may be adjusted from the first position to a different, second position by rotating the C-shaped portion 103. In one example, the second position may be a position in which the x-ray unit 108 and detector 130 are rotated 180 degrees together relative to the first position, such that the x-ray unit 108 is positioned vertically above the detector 130, with axis 166 intersecting the midpoint of the outlet of the x-ray unit 108 and the midpoint of the detector surface 113 of the detector 130. When adjusted to the second position, the x-ray unit 108 may be positioned vertically above the rotational axis 164 of the C-shaped portion 103 of the C-arc 102, and the detector 130 may be positioned vertically below the rotational axis 164. Different rotational positions of the C-arc 102 are possible.

The x-ray unit 108 may include an x-ray tube that includes a cathode that emits a stream of electrons in response to heat resulting from an applied voltage, and an anode including a target that is impacted by the stream of electrons to generate x-rays (e.g., to perform one or more x-ray exposures on a patient of the imaging system). The voltage is applied at a gridding electrode of the cathode to switch the cathode on (e.g., a bias voltage to generate the x-rays) or off (e.g., a grid voltage to stop generation of the x-rays). The cathode may be bipolar, where the gridding voltage is of a first polarity (e.g., negative) and the bias voltage is of an opposite polarity (e.g., positive), or the cathode may be unipolar, where both the gridding voltage and the bias voltage are of a single polarity (e.g., negative).

Voltage changes for switching the cathode on and off may be generated by driving electronics of the cathode that are connected through a cable, e.g., cable 161. It is to be appreciated that cable 161 may include a plurality of individual cables bundled within a common housing. When the cathode of the x-ray tube is unipolar (e.g., monopolar), the cable 161 includes one high voltage (HV) cable to deliver the gridding and bias voltages, rather than two separate cables. The HV cable thus demands a strong isolation and is thicker and has higher stiffness and limited capability for torsion and flexion relative to the cables utilized when the cathode is bipolar. Thus, a different cable may be used when the cathode is uni/monopolar, and as such the HV cable for the monopolar cathode may be referred to as a monopolar cable. The use of a monopolar cathode and corresponding monopolar cable may provide higher image quality than systems that rely on a bipolar tube. Because the C-arc rotates around the patient to take the images as explained above, the cable 161 is mobile and it may be desirable to minimize cable movement in order to keep the cable out of the patient vicinity, thereby avoiding problems of visibility, ergonomics, and sterility. Further, the cable movement may be compatible with the limited capability of torsion and flexion. Accordingly, previous approaches for housing the cables of an imaging system may be unsuitable and lead to degradation of the HV cable. For example, a hose housing the cables with no controlled movement may cause degradation of the HV cable due to the stiffness of the HV cable and the various cable bend radii of the HV cable where the HV cable exits the pivot arm, enters the C-arc, and bends between the entry and exit points. For example, at the joint between the cables and the C-arc and/or at the joint between the cables and the pivot arm, the joint may have a relatively high degree of rotation depending on the position of the C-arc (e.g., 175 degrees). Said another way, exposing the HV cable to high degrees of joint rotation, as done in prior systems, may cause degradation of the HV cable.

Thus, according to embodiments disclosed herein, the cables (including a HV cable) of a medical imaging system (e.g., an interventional system such as a C-arc) may be housed in a cable chain that has pivotable joints where the cable chain couples to the medical imaging system, in particular at the C-arc and the pivot arm. The pivotable joints may be configured to rotate through a limited range of angles to allow movement of the cables as the position of the C-arc relative to the pivot arm is adjusted while preventing over-rotation of the joints that can lead to degraded cables. In addition, the pivotable joints may each include a roller to confine the cables to a lower section of an opening formed in the joint, thereby preventing the cables from contacting an upper edge of the opening, where friction between the cables and the surfaces forming the opening may cause cable degradation. Further, the cable chain may include articulating links with limited articulation to allow the cables to bend, but without the cables bending beyond a minimum cable bend radius and without the cable chain entering an interior, patient area of the C-arc.

Figure 2:
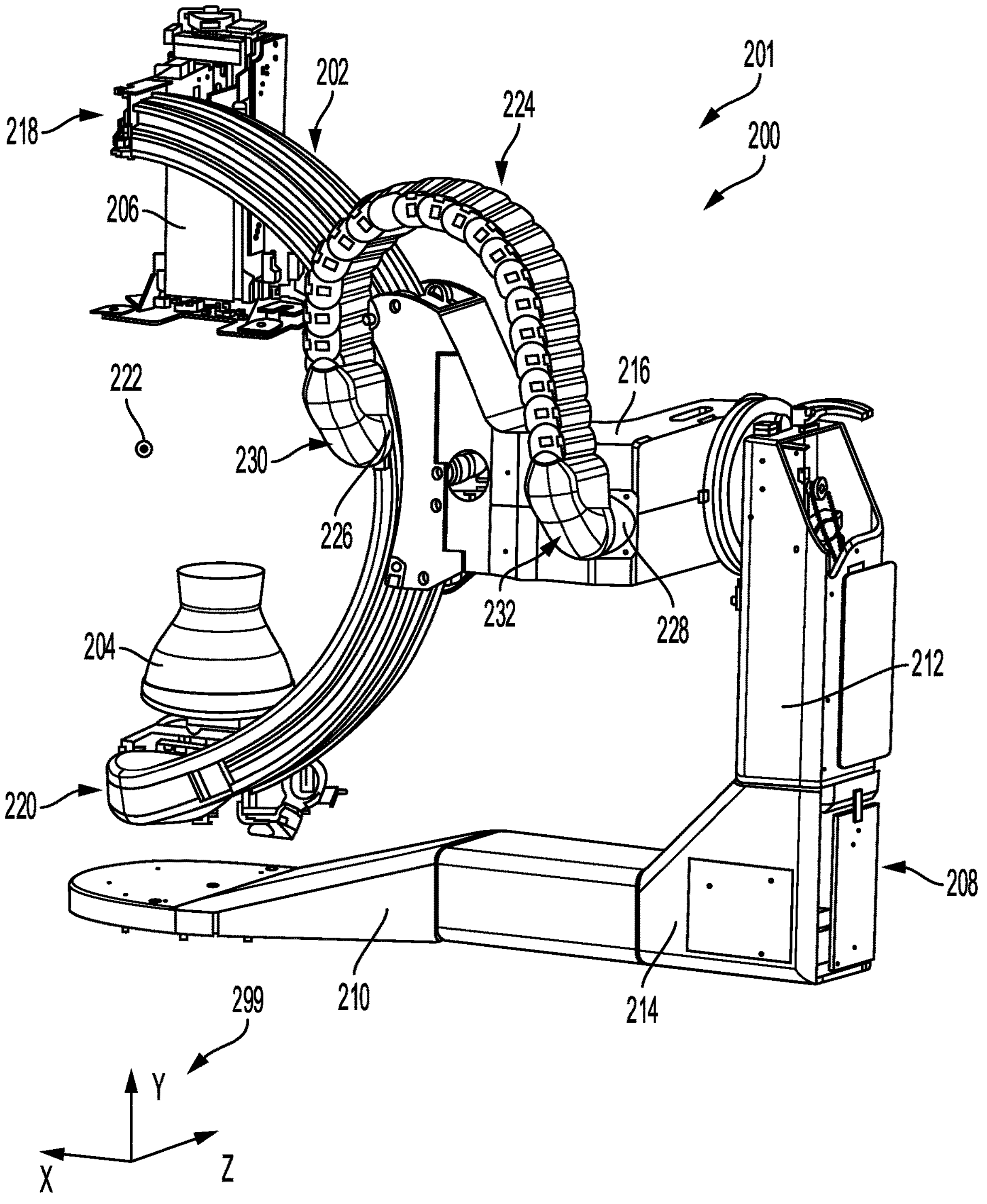
FIGS. 2-4 show various views of a C-arc including a cable chain.

Referring to FIG. 2, a first view 201 (e.g., a side view) of a medical imaging system 200 including a C-arc 202 is shown. The first view 201 includes a Cartesian coordinate system 299, which is also present in FIGS. 3-17 to orient the views. The coordinate system 299 may be relative to the medical imaging system as installed in a medical facility, and includes a y axis that is parallel to gravity, an x axis that extends parallel to a length of a base of the medical imaging system, from the base toward the C-arc, and a z axis that is orthogonal to the y axis and x axis and extends parallel to a width of the base. In the first view 201, external covers of some components of the medical imaging system 200 have been removed to allow visualization of internal components. The medical imaging system 200 is a non-limiting example of imaging system 100 of FIG. 1 and includes a radiation source 204, which may be an x-ray unit, in some examples. The radiation source 204 is positioned opposite to detector 206 and may be configured to emit x-ray radiation. As described above, the radiation source 204 may include an x-ray tube including a monopolar cathode. The medical imaging system 200 additionally includes a base unit 208 supporting the medical imaging system 200 on a ground surface on which the medical imaging system sits. For example, a base 210 of the base unit 208 may be in face sharing contact with the ground. The base unit 208 may further include an extension 212 and a connecting section 214, where the connecting section is positioned intermediate the base 210 and the extension 212.

The C-arc 202 may be connected to a pivot arm 216, with the pivot arm rotatably coupled to the extension 212 of the base unit 208. The detector 206 is coupled to the C-arc 202 at a first end 218, and the radiation source 204 is coupled to the C-arc at an opposing, second end 220. As an example, the C-arc 202 may be configured to rotate in opposing directions relative to the base unit 208 throughout a relatively wide range of angles (e.g., rotate at least 90 degrees, at least 120 degrees, or at least 160 degrees). The C-arc 202 is rotatable about at least a rotational axis 222 and may additionally rotate about additional axes. The C-arc 202 may be rotated as described above in order to adjust the radiation source 204 and detector 206 (positioned on opposite ends of the C-arc) through a plurality of positions.

The base unit 208 may include the electronic controller (e.g., a control and computing unit) that processes instructions or commands sent from the user input devices during operation of the medical imaging system 200. In some examples, the base unit 208 may also include an internal power source (not shown) that provides electrical power to operate the medical imaging system 200. Alternatively, the base unit 208 may be connected to an external electrical power source to power the medical imaging system 200. A plurality of connection lines (e.g., electrical cables) may be provided to transmit electrical power, instructions, and/or data between the radiation source 204, the detector 206, and the control and computing unit. The plurality of connection lines may transmit electrical power from the electrical power source (e.g., internal and/or external source) to the radiation source 204 and the detector 206. As explained above, the plurality of connection lines may include a HV cable that provides voltage to the cathode. The HV cable may also be referred to as a monopolar cable, as the HV cable may provide voltage to a monopolar cathode.

As explained above, a stiffness of the monopolar cable leads to a limited capability for torsion and flexion. However, the monopolar cable and plurality of connection lines may be mobile during imaging due to the C-arc 202 rotating around a patient to take each image. As such, the monopolar cable and other cables/connection lines may be housed in a cable chain 224 that matches the mechanical and usage constraints (e.g., limited torsion and flexion) of the monopolar cable. In this way, movement of the monopolar cable and plurality of connection lines may be minimized, which may keep the monopolar cable out of the patient vicinity and may improve both visibility ergonomics and sterility. Further, the cable chain 224 may reduce degradation of the monopolar cable and connection lines.

The cable chain 224 may be coupled to the medical imaging system 200 at specific attachment points, such as a C-arc joint mount 226 and a pivot arm joint mount 228. The cable chain 224 may include a C-arc joint 230 that is configured to couple with the C-arc joint mount 226, and a pivot arm joint 232 that is configured to couple with the pivot arm joint mount 228. The C-arc joint 230 and the pivot arm joint 232 may be positioned at opposite ends of the cable chain 224, relative to the length of the cable chain. During imaging, positions of cables (e.g., electrical cables) of the medical imaging system 200 are adjusted. As such, a position and orientation of the cable chain 224 that is accommodating the cables may be adjusted via rotation of the C-arc joint 230 and the pivot arm joint 232. The C-arc joint 230 and the pivot arm joint 232 of the cable chain 224 are configured to reduce joint rotation from approximately 175 degrees to approximately 60 degrees. As such, the C-arc joint 230 and the pivot arm joint 232 may reduce degradation of cables of the medical imaging system 200, leading to increased longevity and reliability. The joints of the cable chain 224 (e.g., the C-arc joint 230 and the pivot arm joint 232) and the joint mounts (e.g., the C-arc joint mount 226 and the pivot arm joint mount 228) are described in greater detail with respect to FIGS. 8-12.

Figure 3:
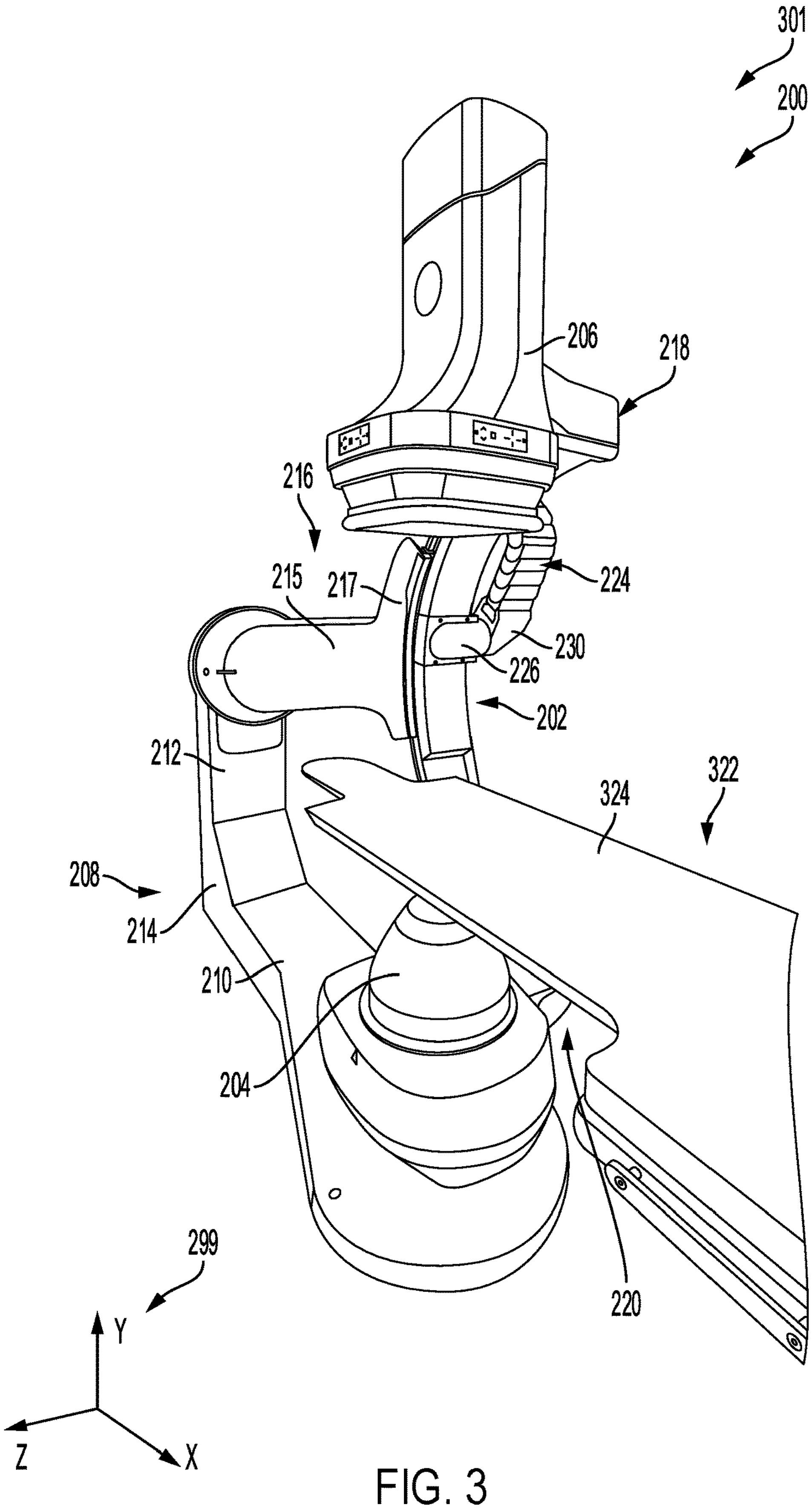
Figure 4:
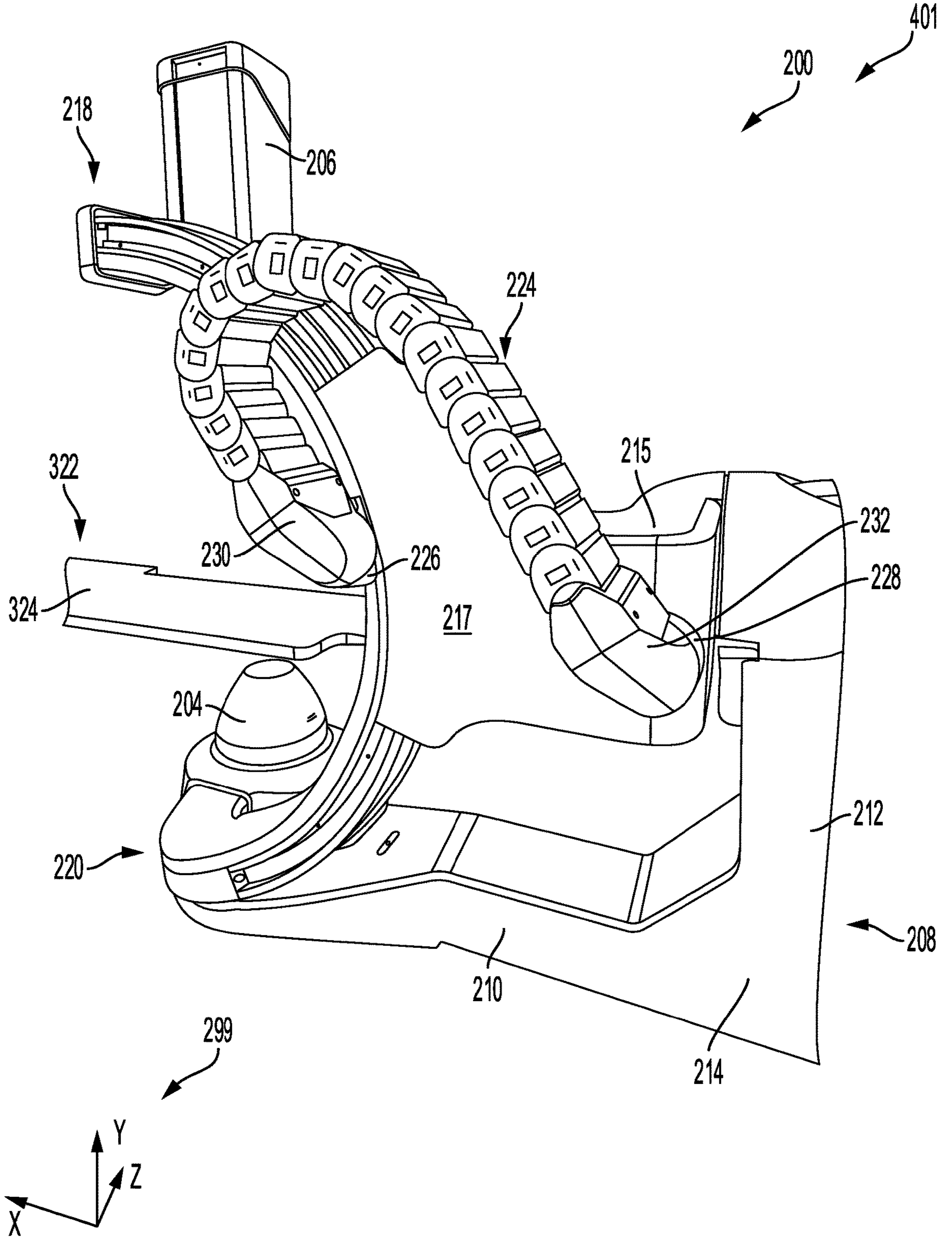

FIGS. 3 and 4 show a second view 301 (e.g., a front view) and a third view 401 (e.g., another side view, opposite to the first view) of the medical imaging system 200, respectively. The pivot arm 216 may be comprised of a horizontal arm 215 and an arced coupling section 217. The horizontal arm 215 may be rotatably coupled to the extension 212 and configured to rotate around a rotational axis that is parallel to the x-axis. The horizontal arm 215 is coupled to the coupling section 217. The coupling section 217 has an arc-shape that matches the arc of the C-arc 202 and is configured to couple to the C-arc 202. The C-arc 202 may include tracks along each side of the C-arc and the coupling section 217 may include protrusions configured to fit within and move relative to the tracks. When the C-arc 202 is rotated as explained above around the axis 222, the protrusions may move within the tracks until the C-arc is at the desired position. The coupling section 217 may include a locking mechanism to lock the coupling section 217 to the C-arc 202 once in the desired position.

As appreciated in FIG. 3, the C-arc joint mount 226 may be coupled to the C-arc 202 at a midpoint of the C-arc 202 between the first end 218 and the second end 220, though other coupling locations may be possible without departing from the scope of this disclosure. The C-arc joint mount 226 may include a cover fixed to an outer (e.g., patient-facing) surface of the C-arc 202. The C-arc 202 may include one or more openings to receive the cables/connection lines housed in the cable chain 224 and the opening(s) may be covered by the cover of the C-arc joint mount 226, in some examples. The C-arc joint mount 226 may further include a mounting extension that extends from the cover, and the mounting extension is configured to couple to the C-arc joint 230. The mounting extension may include an opening to receive the cables/connection lines. In this way, the cable chain 224 may couple to a fixed location on the C-arc 202, via the C-arc joint 230. As the C-arc 202 is rotated relative to the pivot arm 216, the cable chain 224 may move (e.g., bend/extend) and the C-arc joint 230 may rotate relative to the C-arc joint mount 226.

The pivot arm joint 232 may be coupled to the pivot arm joint mount 228. The pivot arm joint mount 228 may be coupled to the pivot arm 216 on a side of the horizontal arm 215 where the horizontal arm 215 transitions to the coupling section 217. The pivot arm joint mount 228 may include an opening to accommodate the cables/connection lines and a mechanism to rotatably mount to the pivot arm joint 232.

As shown in FIGS. 3 and 4, during an imaging operation (e.g., a scan), a portion of a patient's body placed in an opening formed between the radiation source 204 and detector 206 may be irradiated with radiation from the radiation source. For example, a patient may be supported by a patient support table 322, with the patient support table including a support surface 324 and a base, and may be arranged between the radiation source 204 and the detector 206.

As will be explained in more detail below, the cable chain 224 may include a plurality of articulating links. Each link may include a front wall, a back wall, and two side walls that enclose a hollow interior. Each link, other than terminal links at the respective joints, may be coupled to two other links via the side walls in a pivotable manner to allow the links to articulate relative to each other. The hollow interior of the links may form an interior space to accommodate the cables/connection lines.

Referring to FIGS. 5, 6, and 7, the medical imaging system 200 is shown in a first position 501, a second position 601, and a third position 701, respectively.

The C-arc 202 may be adjusted to a plurality of different positions by rotation of the C-arc around the axis 222. For example, in an initial, first position 501 shown by FIG. 5, the radiation source 204 may be positioned vertically below the detector 206, relative to the y-axis. Further, an axis 518 that passes through the radiation source 204 and the detector 206 (e.g., that is perpendicular to the axis 222 that the C-arc 202 rotates around) may be oriented parallel to the y-axis.

The C-arc 202 may be adjusted from the first position 501 to a different, second position 601, as shown in FIG. 6, by rotating the C-arc around the axis 222. In the second position, the radiation source 204 and the detector 206 are rotated approximately 45 degrees around the axis 222 in a first direction (e.g., counter-clockwise), relative to the first position. As such, the axis 518 may be oriented at a 45 degree angle relative to the y-axis and the x-axis. Similarly, the C-arc 202 may be adjusted from the first position or the second position to a different, third position 701, as shown in FIG. 7, by rotating the C-arc around the axis 222. In the third position, the radiation source 204 and the detector 206 are rotated approximately 45 degrees around the axis 222 in a second direction (e.g., clockwise), relative to the first position. When compared to the second position, the radiation source 204 and the detector 206 are rotated approximately 90 degrees around the axis 222 in the second direction (e.g., clockwise). As such, the axis 518 may be oriented at a 45 degree angle relative to the y-axis and the x-axis.

It is to be appreciated that the C-arc 202 may be oriented in positions other than the first position of FIG. 5, the second position of FIG. 6, and the third position of FIG. 7. For example, the C-arc 202 may be rotated to a position that is between the first position and the second position. By rotating the C-arc 202 around the axis 222, the medical imaging system 200 is able to generate three-dimensional images of a subject (e.g., patient).

As the C-arc 202 rotates between positions, positions of cables (e.g., electrical cables) of the medical imaging system 200 are adjusted. As such, a position and orientation of the cable chain 224 that is accommodating the cables may be adjusted via rotation of the C-arc joint 230 and the pivot arm joint 232. The C-arc joint 230 and the pivot arm joint 232 of the cable chain 224 are configured to reduce collective joint rotation from approximately 175 degrees to approximately 60 degrees. This reduced joint rotation may confine the cable chain to extend upwardly from each of the rotatable joints at a plurality of positions. The upward extension of the cable chain can be seen in FIGS. 5, 6, and 7, wherein the angle between the first link in the cable chain and an axis parallel to axis 518 is approximately smaller than 30 degrees in each position shown in FIGS. 5-7. By reducing joint rotation, the cable chain 224, the C-arc joint 230, and the pivot arm joint 232 may cause cables of the medical imaging system 200 to experience reduced degradation, leading to increased longevity and reliability. Further, the cable chain 224 and joints may improve visibility, ergonomics, and sterility in a vicinity of a patient being imaged by the medical imaging system 200.

FIG. 8 shows a magnified view of the pivot arm joint 232 and the pivot arm joint mount 228 of the medical imaging system 200. The pivot arm joint 232 may be coupled to the pivot arm joint mount 228 via mating components, in some examples. The pivot arm joint mount 228 may prevent translational movement of the pivot arm joint 232 while allowing the pivot arm joint to rotate around an axis parallel to the z-axis. In this way, a position of the cable chain 224 may be adjusted as a position of a C-arc (e.g., the C-arc 202 of FIG. 2) is adjusted via rotation of the pivot arm joint 232 on the pivot arm joint mount 228.

The pivot arm joint 232 may include a joint cover 802 which may protect the cables (e.g., electrical cables/connection lines) positioned within the pivot arm joint. The joint cover 802 may include a contoured section 804, two side sections, such as the first side section 806, and an annular mounting section 805. The contoured section 804 may have a top portion that is planar (e.g., extends along an x-y plane) and an angled portion that angles inward, toward the pivot arm joint mount 228, along the z axis. The side sections may each be configured lay flush against (e.g., be in face sharing contact with) a side section of a body of the pivot arm joint 232 (the body of the pivot arm joint is not visible in FIG. 8 and will be explained in more detail below). The joint cover 802 may be coupled to the body of the pivot arm joint 232 via attachment devices 808. In some examples, the attachment devices 808 may be bolts, pins, or screws. The annular mounting section 805 may extend from the first side section 806 to the second side section in an annular fashion and may couple to the contoured section 804. The annular mounting section 805 is configured to face/be adjacent to the pivot arm joint mount 228.

The pivot arm joint mount 228 may include a body 810 and a base 812. The body 810 of the pivot arm joint mount 228 may be in face sharing contact with the pivot arm joint 232, and the base 812 of the pivot arm joint mount may be in face sharing contact with the pivot arm 216. In this way, the pivot arm joint mount 228 couples the pivot arm joint 232 of the cable chain 224 to the pivot arm 216 of the medical imaging system 200. The pivot arm joint mount 228 may be coupled to the pivot arm 216 via a plurality of attachment devices 814 that pass through the base 812. The attachment devices 814 may be bolts, screws, or pins, in some examples. The body 810 may be a hollow cylinder that extends out from the base 812 along the z axis and may include mounting features that facilitate coupling of the pivot arm joint 232.

Figure 9:
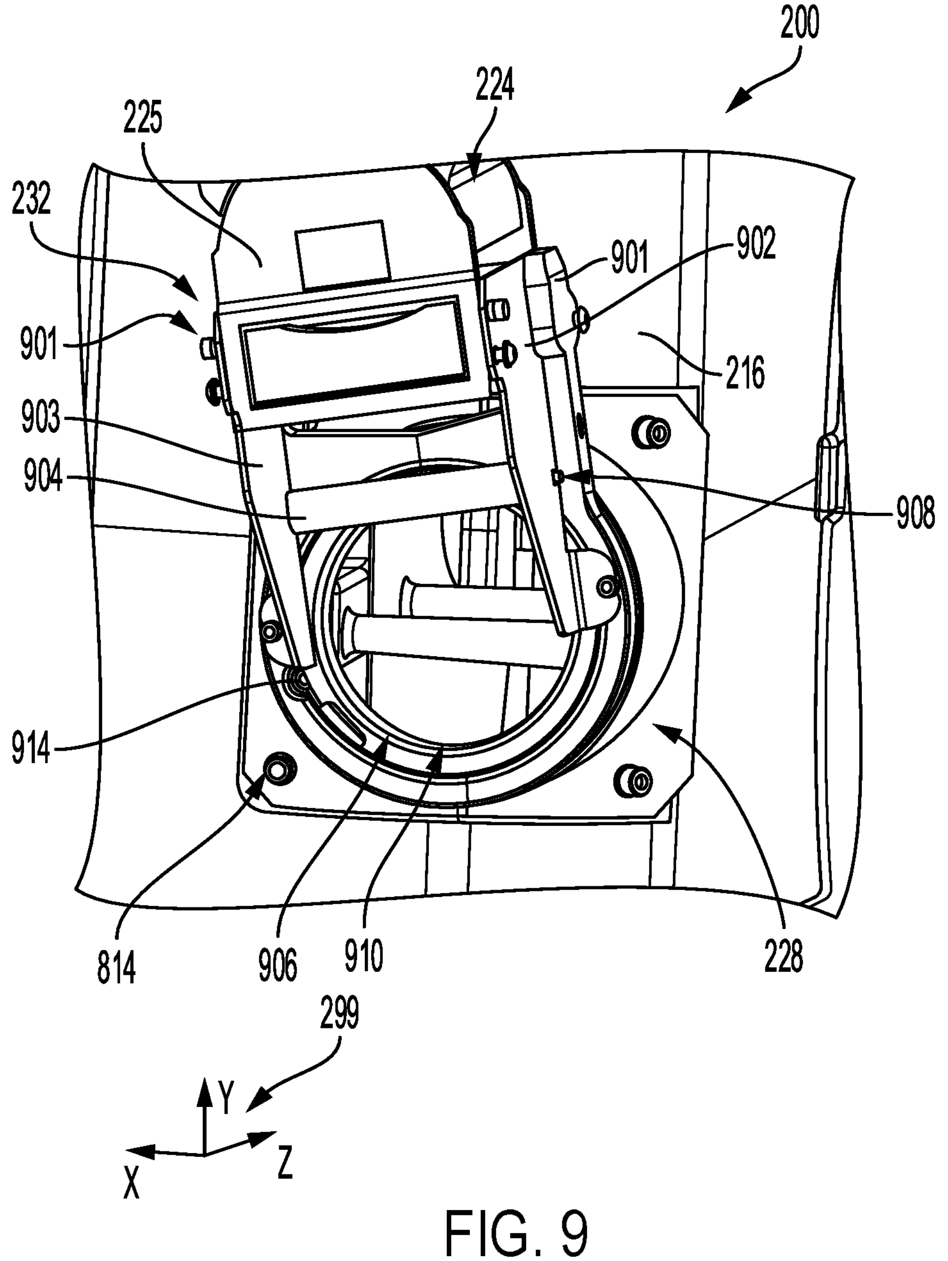
FIG. 9 shows the cable chain joint without a joint cover and the cable chain joint mount of FIG. 8.

FIG. 9 shows the pivot arm joint 232 and the pivot arm joint mount 228 of FIG. 8 without the joint cover 802 to facilitate visualization of the internal components of the pivot arm joint 232. The pivot arm joint 232 may include a body 901 that is housed within the cover 802, as explained above. The body 901 may include an annular mounting section and two side arms that each extend upward from the annular mounting section. The pivot arm joint 232 further includes a first side section 902 and a second side section 903, each of which may be positioned proximate to a respective side section of the joint cover when the joint cover is installed. For example, the first side section 902 of the pivot arm joint 232 may face the first side section 806 of the joint cover 802 of FIG. 8.

The first side section 902 and the second side section 903 may be coupled to the body 901. For example, each side arm of the body 901 may be coupled to a respective side section (e.g., the first side section 902 may be coupled to a first side arm of the body and the second side section 903 may be coupled to a second side arm of the body). Further, each of the first side section 902 and the second side section 903 may have a flange configured to couple to the annular mounting section of the body 901. The pivot arm joint 232 may include surfaces and fastening mechanisms to facilitate coupling of the pivot arm joint to the cable chain 224. For example, a terminating link, referred to as a first link 225, of the cable chain 224 is shown coupled to the first side section 902 and the second side section 903.

The annular mounting section of the body 901, along with the body 810 of the pivot arm joint mount, may define an opening 906 that aligns with an opening 910 of the pivot arm 216. As such, cables accommodated by the cable chain 224 may pass into/out of the pivot arm 216 via the opening 906 and the opening 910. As shown in FIG. 9, the pivot arm joint 232 includes a roller 904 which may be placed closer to the top of opening 906 than the bottom. The roller 904 may prevent or mitigate degradation of cables of the medical imaging system 200. For example, the monopolar cable positioned within the cable chain 224 may be configured to press against the roller 904 instead of an inner edge of an opening 906 of the pivot arm joint mount 228. For example, when the monopolar cable is positioned within the pivot arm joint 232, the monopolar cable may be positioned vertically below the roller 904 relative to the y-axis, which may prevent the monopolar cable from contacting a top of the inner edge of the opening 906. The roller 904 has a cylindrical shape, with a longitudinal axis that may extend from the first side section 902 to the second side section 903. A plurality of attachment devices 908 may couple the roller 904 to the first side section 902 and the second side section 903. The plurality of attachment devices 908 may be bolts, screws, or pins, in some examples. Further, in some examples, the roller 904 may be free to rotate around the longitudinal axis of the roller. As such, friction between cables and the roller 904 may be further reduced.

The pivot arm joint mount 228 may be coupled to the pivot arm 216 via the plurality of attachment devices 814. Further the pivot arm joint 232 may be coupled to the pivot arm joint mount 228 via a lip 1124 of the pivot arm joint mount (shown in FIG. 11 and explained in more detail below) that is configured to mate with the pivot arm joint. For example, the lip of pivot arm joint mount 228 may fit within a slot in the pivot arm joint 232. As such, translation of the pivot arm joint 232 relative to the pivot arm joint mount 228 may be prevented while allowing rotation of the pivot arm joint around an axis parallel to the z-axis. Rotation of the pivot arm joint 232 may be limited by a limiting device 914, which may be a bolt or a pin, in some examples.

Figure 10:
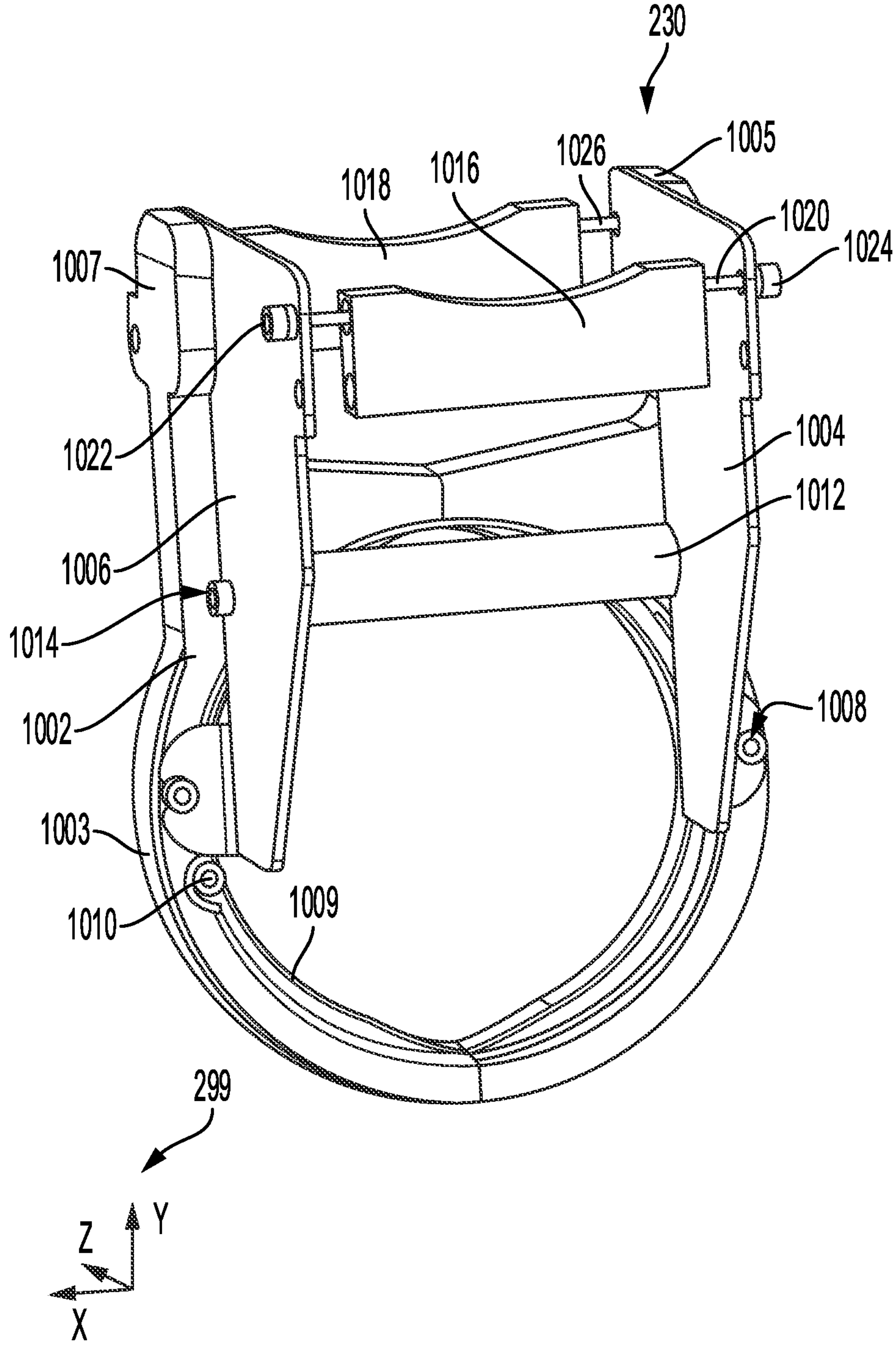
FIG. 10 shows a cable chain joint.

FIG. 10 shows the C-arc joint 230 of FIG. 2, which may be the same in structure and function as the pivot arm joint 232. As such, the C-arc joint 230 may include a body 1002, a first side section 1004, and a second side section 1006. Further, the C-arc joint 230 may include a plurality of attachment devices 1008 for coupling the body 1002 to the first side section 1004 and the second side section 1006, and a limiting device 1010 for limiting rotational movement of the C-arc joint relative to the C-arc joint mount. The C-arc joint 230 may include a roller 1012 for reducing cable degradation, which is coupled to the first side section 1004 and the second side section 1006 via a plurality of attachment devices 1014.

The body 1002 may include may include an annular mounting section 1003 and two side arms, a first side arm 1005 and a second side arm 1007, that each extend upward from the annular mounting section 1003. The first side arm 1005 may be coupled to the first side section 1004 and the second side arm 1007 may be coupled to the second side section 1006. The annular mounting section 1003 includes a back lip 1009 that, when the C-arc joint 230 is coupled to the C-arc joint mount, is configured to fit within an annular space formed between surfaces of the C-arc joint mount. The limiting device 1010 may be coupled to the back lip 1009. The limiting device 1010 may be a bolt that extends from the back lip 1009 along the z-axis, along the negative z direction.

The C-arc joint 230 may include a first flap 1016 and a second flap 1018. The first flap 1016 may be coupled to the C-arc joint 230 via a rod 1020. The rod 1020 may pass through the first side section 1004 and the second side section 1006 of the C-arc joint 230, and may be held in place by a first end cap 1022 and a second end cap 1024. Similarly, the second flap 1018 may be coupled to the C-arc joint 230 via a rod 1026 and two end caps. Each of the first flap 1016 and the second flap 1018 may be configured to mate with a link of the cable chain 224 of FIG. 2 (e.g. a terminal link).

Thus, the first side section 1004 and the second side section 1006 may provide structure for mounting of the cable chain to the C-arc joint and transmit motion of the cable chain 224 and/or motion of the cables/connection lines to the annular mounting section 1003. The first side section 1004 and the second side section 1006 may also provide structure for positioning of the roller 1012 at a desired position relative to the opening formed by the annular mounting section 1003, e.g., in front of the opening (wherein the opening is positioned behind the roller in the positive z direction) and closer to a top of the opening than a bottom of the opening.

Figure 11:
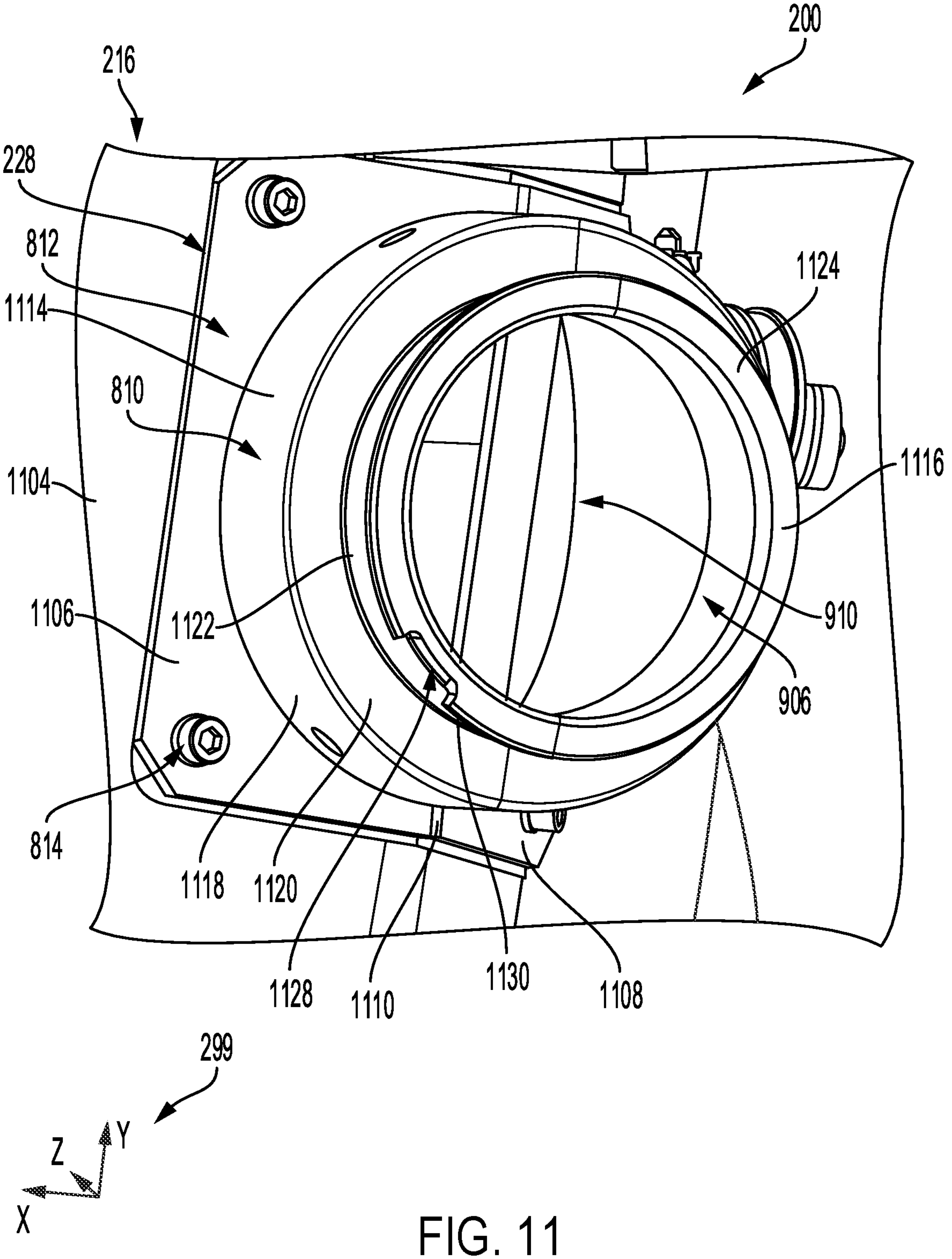
FIG. 11 shows a cable chain joint mount on a pivot arm of the medical imaging system.

FIG. 11 shows the pivot arm joint mount 228 of FIG. 9 uncoupled from a pivot arm joint (e.g., the pivot arm joint 232 of FIG. 9). The pivot arm joint mount 228 includes the opening 906 that aligns with the opening 910 of the pivot arm 216. The pivot arm joint mount 228 may be coupled to the pivot arm 216 via the plurality of attachment devices 814. The attachment devices 814 may be bolts, screws, or pins, in some examples. The attachment devices 814 may pass through the base 812 of the pivot arm joint mount 228 and through an outer surface 1104 of the pivot arm 216. The base 812 of the pivot arm joint mount 228 may be bent. For example, the base 812 may include a first section 1106, a second section 1108, and a bend 1110, where the bend is positioned intermediate the first section and the second section. Each of the first section 1106 and the second section 1108 may be flat (e.g., planar) and the bend 1110 may allow the first section and the second section to lay flat against (e.g., be in face sharing contact with) the outer surface 1104 of the pivot arm 216.

The body 810 of the pivot arm joint mount 228 includes a housing section 1114 and a mating section 1116, where the housing section is positioned intermediate the mating section and the base 812. The housing section 1114 may be cylindrical, and may be configured to accommodate cables passing through the pivot arm joint mount 228. Further, the housing section 1114 may be positioned closer to the pivot arm 216 than the mating section 1116. The housing section 1114 may include an outer circumferential surface 1118 and a flat surface 1120. When a pivot arm joint is coupled to the pivot arm joint mount 228, the flat surface 1120 may be in face sharing contact with a surface of the pivot arm joint. The flat surface 1120 may be planar in an x-y plane. It is to be appreciated that in examples where the base 812 is bent, as explained above, the outer circumferential surface 1118 may be longer (e.g., in a direction along the z-axis) at the sides away from the bend 1110 than at the top and bottom near the bend 1110.

The mating section 1116 may be configured to mate with a pivot arm joint (e.g., the pivot arm joint 232 of FIG. 2) and may include a body 1122 and the lip 1124. The body 1122 may be annular and extend outward along the z-axis from the flat surface 1120. The lip 1124 may be positioned along an edge of the body 1122, where the edge is distal the housing section 1114. Further, the lip 1124 may extend outwards, away from the opening 906, from a circumferential surface of the body 1122, parallel to the x-y plane, to thereby overhang the body 1122. The lip 1124 may mate with a slot in the pivot arm joint, in some examples. For example, the lip 1124 may be positioned within and/or against the pivot arm joint in such a way that prevents translational movement of the pivot arm joint while allowing rotational movement.

The lip 1124 includes a slot 1128, also referred to as a notch, which may extend inwards from an outer circumferential edge 1130 of the lip. The slot 1128 may extend inward approximately 75% of the way from the outer circumferential edge 1130 to the opening 906. Further, the slot 1128 may extend along a length of the outer circumferential edge 1130 of the mating section 1116. In some examples, the slot 1128 may extend approximately 5-10% of the way around the outer circumferential edge 1130.

The slot 1128 is configured to mate with the limiting device 914 of the pivot arm joint 232 of FIG. 9. The limiting device 914 may be positioned within the slot 1128, and may move within the slot when the pivot arm joint 232 rotates. For example, the limiting device 914 may translate along a length of the slot 1128 as the pivot arm joint 232 rotates during a repositioning of a C-arc of the medical imaging system 200. The slot 1128 may limit a range of motion of the limiting device, and may therefore limit rotation of the pivot arm joint. By limiting rotation of the pivot arm joint, the slot 1128 and limiting device 914 may reduce bending and/or movement of cables passing through the pivot arm joint mount 228, thereby reducing degradation of the cables.

Figure 12:
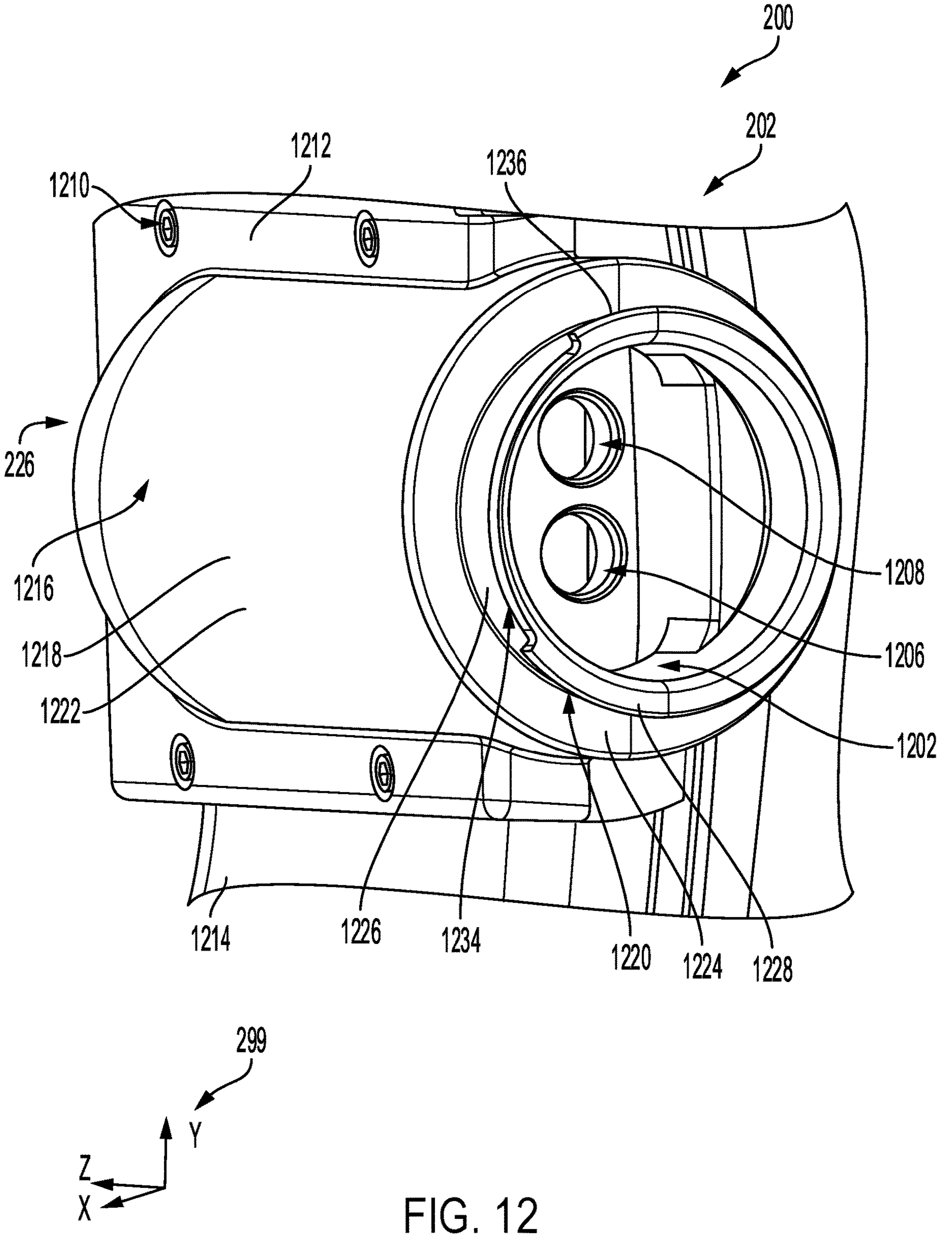
FIG. 12 shows a cable chain mount on the C-arc of the medical imaging device.

FIG. 12 shows a magnified view of the C-arc 202 including the C-arc joint mount 226 of FIG. 2. The C-arc joint mount 226 includes an opening 1202 that aligns with a first inner opening 1206 and a second inner opening 1208 of the C-arc 202. As such, cables accommodated by the cable chain 224 may pass into/out of the C-arc 202 via the opening 1202 and the first inner opening 1206 and/or the second inner opening 1208. For example, cable(s) coupled to the detector may pass through the second inner opening 1208 and cable(s) coupled to the radiation source may pass through the first inner opening 1206. In this way, electrical signals may be carried from the C-arc 202 (and specifically the radiation source and the detector) to the base 208 via the pivot arm 216 of the medical imaging system 200, and vice versa, via one or more cables. Alternatively, the first inner opening 1206 and the second inner opening 1208 may be voids formed on a guide plate of the C-arc joint mount 226 and the cables may pass through one or more openings of the C-arc formed on an outer surface 1214 of the C-arc, as explained previously.

The C-arc joint mount 226 may be coupled to the C-arc 202 via a plurality of attachment devices 1210. The attachment devices 1210 may be bolts, screws, or pins, in some examples. The attachment devices 1210 may pass through a base 1212 of the C-arc joint mount 226 and through an outer surface 1214 of the C-arc 202. The base 1212 of the C-arc joint mount 226 may extend outwards from a cylindrical body 1216 of the C-arc joint mount from three sides. For example, the base 1212 may extend outwards from the cylindrical body 1216 in two directions parallel to the y-axis (e.g., above and below) and one direction parallel to the z-axis. A bottom surface of the base 1212 may be configured to lay flat against (e.g., be in face sharing contact with) the outer surface 1214 of the C-arc 202.

The cylindrical body 1216 of the C-arc joint mount 226 includes a housing section 1218 and a mating section 1220, where the housing section 1218 is positioned intermediate the mating section 1220 and the base 1212. Further, the base 1212 may extend from the housing section 1218. The housing section 1218 may be cylindrical, in some examples. In other examples, the housing section 1218 may include a cylindrical surface and a domed surface, with the domed surface positioned distal to the mating section 1220 of the body 1216. Further, the housing section 1218 may be positioned closer to the C-arc 202 than the mating section 1220. The housing section 1218 may include an outer circumferential surface 1222 and a flat surface 1224. When a C-arc joint is coupled to the C-arc joint mount 226, the flat surface 1224 may face and/or be adjacent to a surface of the C-arc joint. In some examples, the flat surface 1224 may be in face-sharing contact with the surface of the C-arc joint. The flat surface 1224 may be planar in an x-y plane The mating section 1220 may be configured to mate with a C-arc joint (e.g., the C-arc joint 230 of FIG. 2) and may include a body 1226 that extends outward, along the z-axis, from the flat surface 1224 and a lip 1228. The lip 1228 may be positioned along an edge of the body 1226, where the edge is distal the housing section 1218. Further, the lip 1228 may extend outwards from a circumferential surface of the body 1226, parallel to the x-y plane. The lip 1228 may mate with a slot in the C-arc joint, in some examples. For example, the lip 1228 may be positioned within and/or against the C-arc joint in such a way that prevents translational movement of the C-arc joint while allowing rotational movement. Further, a space formed between the flat surface 1224 and a back side of the lip 1228 may accommodate a corresponding lip of the C-arc joint, e.g., the back lip 1009.

The lip 1228 includes a slot 1234, also referred to as a notch, which may extend inwards from an outer circumferential edge 1236 of the lip. The slot 1234 may extend inward approximately 75% of the way from the outer circumferential edge 1236 to the opening 1202. Further, the slot 1234 may extend along a length of the outer circumferential edge 1236 of the mating section 1220. In some examples, the slot 1234 may extend approximately 25% of the way around the outer circumferential edge 1236.

The slot 1234 is configured to accommodate a limiting device of a C-arc joint, such as limiting device 1010, similarly to the slot 1128 and the limiting device 914 of FIG. 11 and FIG. 9, respectively. As such, a limiting device may be positioned within the slot 1234, and may move within the slot when a C-arc joint rotates. For example, the limiting device may translate along a length/arc of the slot 1234 as the C-arc joint rotates during a repositioning of the C-arc 202. The lip 1228, at the edges that form the slot 1234, may limit a range of motion of the limiting device, and may therefore limit rotation of the C-arc joint. As such, the length of the slot 1234 may be selected to reduce bending and/or movement of cables passing through the C-arc joint mount 226, thereby reducing degradation of the cables. It is to be appreciated that the slot 1234 of the C-arc joint mount 226 may be longer than the slot 1128 of the pivot arm joint mount 228. As such, the C-arc joint may rotate a greater amount than the pivot arm joint. Accordingly, the C-arc joint is rotatable relative to the C-arc joint mount throughout a first range of angles defined by a first slot in the C-arc joint mount and a first limiting device of the C-arc joint, and the pivot arm joint is rotatable relative to the pivot arm joint mount throughout a second range of angles defined by a second slot in the pivot arm joint mount and a second limiting device of the pivot arm joint. In some examples, the first range of angles is larger than the second range of angles.

FIG. 13 shows a portion of a pivot arm joint 1302 and a pivot arm joint mount 1304 accommodating a plurality of cables 1306. The pivot arm joint 1302 is a non-limiting example of the pivot arm joint 232 and the pivot arm joint mount 1304 is a non-limiting example of the pivot arm joint mount 228. The cables 1306 may extend from behind a flap 1308 of a cable chain 1310 and into the portion of the pivot arm joint 1302 (e.g., in between the first flap and the second flap of the pivot arm joint). The cables 1306 may then extend from the portion of a pivot arm joint 1302 through an opening 1312 in the pivot arm joint 1302 and pivot arm joint mount 1304 and into a pivot arm 1314. A roller 1316 is in face sharing contact with one or more cables of the plurality of cables 1306, and may prevent the cables from rubbing against an edge of the opening 1312. In particular, the cables 1306 are positioned in front of the roller 1316 relative to the z axis and extend under the roller 1316, such that the cables 1306 are positioned between the roller 1316 and a bottom portion 1305 of a lip 1303 of the pivot arm joint mount 1304. As such, the roller 1316 may reduce degradation of the cables 1306. Further, a limiting device 1318 is positioned in a slot 1320 in the pivot arm joint mount 1304, and may limit rotation of the portion of a pivot arm joint 1302 relative to the pivot arm joint mount. This may include limiting the position of a pivot arm joint to a narrow range of angles surrounding 0 degrees where 0 degrees represents alignment with the y-axis. The alignment of a plurality of cables 1306 contained within the pivot arm joint 1302 and extend into the pivot arm joint mount 1304 is dictated by this angle. This may allow the cable chain to extend upwardly from the pivot arm joint 1302 at a plurality of C-arc positions. In this way, the limiting device 1318 and slot 1320 may increase the turn radius of cables 1306. This reduces wear on the cables increasing their longevity and reliability.

FIG. 14 shows the cable chain 224 of the medical imaging system 200 of FIG. 2. The cable chain 224 includes the pivot arm joint 232 and the C-arc joint 230, each without a joint cover (e.g., the joint cover 802 of FIG. 8). The pivot arm joint 232 is coupled to the pivot arm joint mount 228, and the C-arc joint 230 is coupled to the C-arc joint mount 226. The C-arc joint 230 includes the roller 1012 and the pivot arm joint 232 includes the roller 904.

The cable chain 224 may include a plurality of links 1406, with each link coupled to neighboring links. The first link 225 of the cable chain 224 may be coupled to the pivot arm joint 232 and a second link 1410 of the cable chain may be coupled to the C-arc joint 230. The cable chain 224 may be oriented such the first link 225 extends upwards from the pivot arm joint 232 and the second link 1410 extends upwards from the C-arc joint 230, relative to the y-axis. In this way, the cable chain 224 may be kept away from the vicinity of a patient being imaged, increasing the sterility and visual ergonomics of the medical imaging system 200.

The first link 225 may be coupled to a first intermediate link 1412, which in turn is coupled to a second intermediate link 1414. The first intermediate link 1412 and second intermediate link 1414, as well as the remaining intermediate links (e.g., the other links besides the second link 1410), may be coupled to two neighboring links. Each link may be coupled to a neighboring link via a pivotable/articulating interlocking mechanism. For example, the first intermediate link 1412 may include a female end configured to interlock/mate with a male end of the second intermediate link 1414. The first intermediate link 1412 may also include a male end configured to interlock/mate with a female end of the first link 225. The interlocking mechanisms may be joined via snap-fit or other suitable interlocking mechanism. As explained previously, each link may include four sides to enclose a hollow interior, with a top and bottom of each link being open to allow the cables to pass through each link.

In some examples, the plurality of links 1406 may have limited rotation/articulation in one or more angular directions (e.g., clockwise and/or counter-clockwise) to allow the cable chain 224 to remain in a substantially straight position near the C-arc at certain positions of the C-arc, such as the positions shown in FIGS. 5 and 7. In doing so, the cable chain 224 is maintained outside an interior region of the C-arc 202. For example, the plurality of links 1406 may include links, such as the second link 1410, a third intermediate link 1416, and a fourth intermediate link 1418, that are configured to rotate/pivot through a limited range of angles. In some examples, the second link 1410 may not be configured to rotate, and the range of angles for the other links may include 0-90 degrees, with 0 degrees being aligned with a vertical axis of the C-arc joint 230 (e.g., aligned with the y-axis) and 90 degrees being a rotation of 90 degrees relative to the 0 degrees in a first direction (e.g., a clockwise direction), from the view of FIG. 14. In the example that the second link 1410 is not configured to rotate, the link may be approximately aligned with the vertical axis of the C-arc joint 230. This may lead the cable chain to extend upwardly from the C-arc joint at a plurality of arc positions, as shown in FIGS. 5, 6, and 7, wherein the second link remains within approximately 30 degrees of the C-arc joint in a plurality of C-arc positions. In some examples, the third intermediate link 1416 and the fourth intermediate link 1418 may be able to rotate freely in the first angular direction but may be stopped from rotating beyond 0 degrees when rotating in a second angular direction (e.g., a counter-clockwise direction). It is to be appreciated that other links of the plurality of links 1406 may be similarly limited in rotation, or other links may not be limited in rotation. By limiting link rotation, the cable chain 224 may bend to accommodate different positions of the C-arc while maintaining a cable bend radius above a threshold radius (e.g., where, below the threshold radius, cable degradation may occur) and while preventing the cable chain 224 from entering an interior region of the C-arc (which may be defined as the space from the outer surface of the C-arc to at least the radiation source and the detector).

FIG. 15 shows a first view of the cable chain 224 of FIG. 2 including the pivot arm joint 232 and the C-arc joint 230. FIGS. 16 and 17 show a second view and a third view of the cable chain 224, respectively. The cable chain 224 has been removed from the medical imaging system 200 to better illustrate components of the cable chain. FIGS. 15-17 are described collectively herein.

The pivot arm joint 232 is positioned at first end 1502 of the cable chain 224. The C-arc joint 230 is positioned at a second end 1504 of the cable chain 224, where the second end is opposite the first end 1502, relative to the length of the cable chain. Further, the pivot arm joint 232 is coupled to the first link 225 of the cable chain 224 and the C-arc joint 230 is coupled to the second link 1410 of the cable chain. The cable chain 224 includes the plurality of links 1406, where every link that is not the first link 1408 or the second link 1410 is positioned between the first link and the second link along the length of the cable chain.

Each link of the plurality of links 1406, such as the second intermediate link 1414, may be identical, in some examples. Each link may be comprised of a series of faces surrounding a hollow interior capable of containing cables in electrical communication with the radiation source and/or detector. Each link includes a front face 1508 and a back face 1510, where the back face is positioned opposite the front face, relative to the z-axis. Each of the front face 1508 and the back face 1510 may have a flat profile, parallel to the x-y plane. Each link further includes a first side 1512 and a second side (the second side of the second intermediate link 1414 is not shown, though the second sides of the third intermediate link 1416 and the fourth intermediate link 1418 are shown), where the second side is positioned opposite the first side, relative to the x-axis. The first side 1512 of the link may be configured to mate with (e.g., couple to) a first side of each neighboring link of the cable chain 224. Similarly, the second side of the link may be configured to mate with a second side of each neighboring link of the cable chain 224. In this way, the plurality of links 1406 may be coupled together in such a way that allows the cable chain 224 to be flexible. For example, the cable chain 224 may bend at the coupling point of each first side and/or second side of neighboring links. As such, the cable chain 224 may be flexible with each link having a respective rotational axis that extends parallel to the z axis and being configured to rotate through a potentially limited range of angles. Further, the cable chain 224 may not be configured to bend towards and/or away from the front faces and back faces of the plurality of links 1406. This configuration may prevent the links from rotating around the x or y axes and may prevent the cable chain from entering an interior region of the C-arc.

The C-arc joint 230 may include the first flap 1016 and the second flap 1018 of FIG. 10. Each of the first flap 1016 and the second flap 1018 may be coupled to the C-arc joint 230 via a rod. Similarly, the pivot arm joint 232 may include a first flap and a second flap each coupled to the pivot arm joint via a rod. Each of the flaps and rods may be configured to mate with one of the plurality of links 1406 of the cable chain 224. For example, the second link 1410 may couple to the rods of the C-arc joint 230 via slots, hooks, or a similar coupling method. Further, at least a portion of each of the first flap 1016 and the second flap 1018 may be in face sharing contact with the second link 1410 such that the first flap and second flap may be positioned on opposite sides of the second link.

Thus, a cable management system for a medical imaging system is disclosed herein. The cable management system may include a cable chain including a plurality of articulating links, the cable chain having a hollow interior configured to house one or more electrical cables. The cable management system may further include a first joint coupled to a first end of the cable chain and a second joint coupled to a second end of the cable chain, a first joint mount configured to couple the first joint to a first component of a medical imaging system, and a second joint mount configured to couple the second joint to a second component of the medical imaging system. The first joint may include a first limiting device configured to limit rotation of the first joint to a first range of angles relative to the first joint mount and the second joint may include a second limiting device configured to limit rotation of the second joint to a second range of angles relative to the second joint mount. The first component of the medical imaging system may be a C-arc/C-shaped gantry housing a radiation source and a radiation detector, at least in some examples. The second component of the medical imaging system may be a pivot arm configured to rotate the C-arc.

The technical effect of a medical imaging system that includes a C-arc, a cable chain, and two cable chain joints is that visibility ergonomics and sterility may be improved in a vicinity of a patient during imaging. Further, a monopolar cable within the cable chain may improve image quality of the medical imaging system, and limited rotation of the cable chain joints may reduce degradation of the monopolar cable.

The disclosure also provides support for a medical imaging system, comprising: a C-arc, a radiation source coupled to a first end of the C-arc, a detector coupled to a second end of the C-arc, opposite to the radiation source, and configured to receive radiation from the radiation source, a pivot arm configured to adjust a position of the C-arc, and a cable chain coupled to each of the C-arc and the pivot arm via rotatable joints, wherein the cable chain extends upwardly from each of the rotatable joints at each of a plurality of positions of the C-arc. In a first example of the system, the cable chain is configured to house one or more cables, the one or more cables in electrical communication with the radiation source and/or detector. In a second example of the system, optionally including the first example, the rotatable joints include a C-arc joint and a pivot arm joint. In a third example of the system, optionally including one or both of the first and second examples, the C-arc joint is coupled to the C-arc via a C-arc joint mount and the pivot arm joint is coupled to the pivot arm via a pivot arm joint mount. In a fourth example of the system, optionally including one or more or each of the first through third examples, the C-arc joint is rotatable relative to the C-arc joint mount throughout a first range of angles, the first range of angles defined by a first slot in the C-arc joint mount and a first limiting device of the C-arc joint, and wherein the pivot arm joint is rotatable relative to the pivot arm joint mount throughout a second range of angles, the second range of angles defined by a second slot in the pivot arm joint mount and a second limiting device of the pivot arm joint. In a fifth example of the system, optionally including one or more or each of the first through fourth examples, the first range of angles is larger than the second range of angles. In a sixth example of the system, optionally including one or more or each of the first through fifth examples, the C-arc joint includes a first annular mounting section defining a first opening and the pivot arm joint includes a second annular mounting section defining a second opening. In a seventh example of the system, optionally including one or more or each of the first through sixth examples, the C-arc joint includes a first roller positioned in front of the first opening and the pivot arm joint includes a second roller positioned in front of the second opening. In an eighth example of the system, optionally including one or more or each of the first through seventh examples, the first roller is positioned closer to a top of the first opening than a bottom of the first opening and the second roller is positioned closer to a top of the second opening than a bottom of the second opening. In a ninth example of the system, optionally including one or more or each of the first through eighth examples, the cable chain includes a plurality of articulating links, and wherein one or more articulating links of the plurality of articulating links has limited rotation in a first angular direction.

The disclosure also provides support for a cable management system, comprising: a cable chain including a plurality of articulating links, the cable chain having a hollow interior configured to house one or more electrical cables, a first joint coupled to a first end of the cable chain and a second joint coupled to a second end of the cable chain, a first joint mount configured to couple the first joint to a first component of a medical imaging system, a second joint mount configured to couple the second joint to a second component of the medical imaging system, wherein the first joint includes a first limiting device configured to limit rotation of the first joint to a first range of angles relative to the first joint mount and the second joint includes a second limiting device configured to limit rotation of the second joint to a second range of angles relative to the second joint mount. In a first example of the system, the first joint includes a first annular mounting section defining a first opening, the first opening configured to accommodate the one or more electrical cables, wherein the first annular mounting section includes the first limiting device, wherein the first joint mount includes a first lip having a first slot, and the first limiting device is configured to move within the first slot and limit rotation of the first joint via contact with the first lip at respective edges of the first slot. In a second example of the system, optionally including the first example, the first joint includes a first roller positioned in front of the first annular mounting section. In a third example of the system, optionally including one or both of the first and second examples, the first range of angles is different than the second range of angles.

The disclosure also provides support for a medical imaging system, comprising: a C-arc including a radiation source coupled to a first end of the C-arc and a detector coupled to a second end of the C-arc, opposite to the radiation source, a base, a cable coupled to the base and to the radiation source and passing through the C-arc and a pivot arm configured to move the C-arc, and a cable chain coupled to the pivot arm via a pivot arm joint and coupled to the C-arc via a C-arc joint, the cable chain configured to house the cable. In a first example of the system, the cable chain extends upwardly from each of the C-arc joint and the pivot arm joint at each of a plurality of positions of the C-arc. In a second example of the system, optionally including the first example, the cable chain includes a plurality of articulating links, and wherein one or more articulating links of the plurality of articulating links has limited rotation in a first angular direction. In a third example of the system, optionally including one or both of the first and second examples, the C-arc joint is coupled to the C-arc via a C-arc joint mount and the pivot arm joint is coupled to the pivot arm via a pivot arm joint mount, wherein the C-arc joint is rotatable relative to the C-arc joint mount throughout a first range of angles, the first range of angles defined by a first slot in the C-arc joint mount and a first limiting device of the C-arc joint, and wherein the pivot arm joint is rotatable relative to the pivot arm joint mount throughout a second range of angles, the second range of angles defined by a second slot in the pivot arm joint mount and a second limiting device of the pivot arm joint. In a fourth example of the system, optionally including one or more or each of the first through third examples, the first range of angles is larger than the second range of angles. In a fifth example of the system, optionally including one or more or each of the first through fourth examples, the C-arc joint includes a first annular mounting section defining a first opening and the pivot arm joint includes a second annular mounting section defining a second opening, and wherein the C-arc joint includes a first roller positioned in front of the first opening and the pivot arm joint includes a second roller positioned in front of the second opening.

As used herein, the term “approximately” is construed to mean plus or minus five percent of the range unless otherwise specified.

As used herein, an element or step recited in the singular and preceded with the word “a” or “an” should be understood as not excluding plural of said elements or steps, unless such exclusion is explicitly stated. Furthermore, references to “one embodiment” of the present invention are not intended to be interpreted as excluding the existence of additional embodiments that also incorporate the recited features. Moreover, unless explicitly stated to the contrary, embodiments “comprising,” “including,” or “having” an element or a plurality of elements having a particular property may include additional such elements not having that property. The terms “including” and “in which” are used as the plain-language equivalents of the respective terms “comprising” and “wherein.” Moreover, the terms “first,” “second,” and “third,” etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A medical imaging system, comprising:

a C-arc;

a radiation source coupled to a first end of the C-arc;

a detector coupled to a second end of the C-arc, opposite to the radiation source, and configured to receive radiation from the radiation source;

a pivot arm configured to adjust a position of the C-arc; and a cable chain coupled to each of the C-arc and the pivot arm via rotatable joints, wherein the cable chain extends upwardly from each of the rotatable joints at each of a plurality of positions of the C-arc, wherein the cable chain is configured to house one or more cables, the one or more cables in electrical communication with the radiation source and/or detector, wherein the rotatable joints include a C-arc joint and a pivot arm joint, wherein the C-arc joint includes a first annular mounting section defining a first opening and the pivot arm joint includes a second annular mounting section defining a second opening, and wherein the C-arc joint includes a first roller positioned in front of the first opening and the pivot arm joint includes a second roller positioned in front of the second opening.

2. The medical imaging system of claim 1, wherein the C-arc joint is coupled to the C-arc via a C-arc joint mount and the pivot arm joint is coupled to the pivot arm via a pivot arm joint mount.

3. The medical imaging system of claim 2, wherein the C-arc joint is rotatable relative to the C-arc joint mount throughout a first range of angles, the first range of angles defined by a first slot in the C-arc joint mount and a first limiting device of the C-arc joint, and wherein the pivot arm joint is rotatable relative to the pivot arm joint mount throughout a second range of angles, the second range of angles defined by a second slot in the pivot arm joint mount and a second limiting device of the pivot arm joint.

4. The medical imaging system of claim 3, wherein the first range of angles is larger than the second range of angles.

5. The medical imaging system of claim 1, wherein the first roller is positioned closer to a top of the first opening than a bottom of the first opening and the second roller is positioned closer to a top of the second opening than a bottom of the second opening.

6. The medical imaging system of claim 1, wherein the cable chain includes a plurality of articulating links, and wherein one or more articulating links of the plurality of articulating links has limited rotation in a first angular direction.

7. A cable management system, comprising:

a cable chain including a plurality of articulating links, the cable chain having a hollow interior configured to house one or more electrical cables;

a first joint coupled to a first end of the cable chain and a second joint coupled to a second end of the cable chain;

a first joint mount configured to couple the first joint to a first component of a medical imaging system;

a second joint mount configured to couple the second joint to a second component of the medical imaging system, wherein the first joint includes a first limiting device configured to limit rotation of the first joint to a first range of angles relative to the first joint mount and the second joint includes a second limiting device configured to limit rotation of the second joint to a second range of angles relative to the second joint mount.

8. The system of claim 7, wherein the first joint includes a first annular mounting section defining a first opening, the first opening configured to accommodate the one or more electrical cables, wherein the first annular mounting section includes the first limiting device, wherein the first joint mount includes a first lip having a first slot, and the first limiting device is configured to move within the first slot and limit rotation of the first joint via contact with the first lip at respective edges of the first slot.

9. The system of claim 8, wherein the first joint includes a first roller positioned in front of the first annular mounting section.

10. The system of claim 7, wherein the first range of angles is different than the second range of angles.

11. A medical imaging system, comprising:

a C-arc including a radiation source coupled to a first end of the C-arc and a detector coupled to a second end of the C-arc, opposite to the radiation source;

a base;

a cable coupled to the base and to the radiation source and passing through the C-arc and a pivot arm configured to move the C-arc; and a cable chain coupled to the pivot arm via a pivot arm joint and coupled to the C-arc via a C-arc joint, the cable chain configured to house the cable, wherein the C-arc joint is coupled to the C-arc via a C-arc joint mount and the pivot arm joint is coupled to the pivot arm via a pivot arm joint mount, wherein the C-arc joint is rotatable relative to the C-arc joint mount throughout a first range of angles, the first range of angles defined by a first slot in the C-arc joint mount and a first limiting device of the C-arc joint, and wherein the pivot arm joint is rotatable relative to the pivot arm joint mount throughout a second range of angles, the second range of angles defined by a second slot in the pivot arm joint mount and a second limiting device of the pivot arm joint.

12. The medical imaging system of claim 11, wherein the cable chain extends upwardly from each of the C-arc joint and the pivot arm joint at each of a plurality of positions of the C-arc.

13. The medical imaging system of claim 11, wherein the cable chain includes a plurality of articulating links, and wherein one or more articulating links of the plurality of articulating links has limited rotation in a first angular direction.

14. The medical imaging system of claim 11, wherein the first range of angles is larger than the second range of angles.

15. The medical imaging system of claim 11, wherein the C-arc joint includes a first annular mounting section defining a first opening and the pivot arm joint includes a second annular mounting section defining a second opening, and wherein the C-arc joint includes a first roller positioned in front of the first opening and the pivot arm joint includes a second roller positioned in front of the second opening.

* * * * *